US012752078B2

(12) United States Patent
Myrick et al.

(10) Patent No.: US 12,752,078 B2

(45) Date of Patent: Oct. 6, 2026

(54) CATHETERS AND SYSTEMS FOR DIRECT INJECTION OF GAS-ENRICHED LIQUID INTO A PATIENT

(71) Applicant: Zoll Circulation, Inc., San Jose, CA (US)

(72) Inventors: Stephen Myrick, Tustin, CA (US); Jeffrey Creech, Los Angeles, CA (US); Jeremy Dabrowiak, Santa Clara, CA (US); John Buckley, San Jose, CA (US); Masoumeh Mafi, Mountain View, CA (US)

(73) Assignee: Zoll Circulation, Inc., San Jose, CA (US)

( * ) Notice: Subject to any disclaimer, the term of this patent is extended or adjusted under 35 U.S.C. 154(b) by 518 days.

(21) Appl. No.: 18/276,558

(22) PCT Filed: Feb. 18, 2022

(86) PCT No.: PCT/US2022/016988

§ 371 (c)(1),
(2) Date: Aug. 9, 2023

(87) PCT Pub. No.: WO2022/178257

PCT Pub. Date: Aug. 25, 2022

(65) Prior Publication Data

US 2024/0307656 A1 Sep. 19, 2024

Related U.S. Application Data

(60) Provisional application No. 63/151,422, filed on Feb. 19, 2021.

(51) Int. Cl.
*A61M 25/00* (2006.01)
*A61B 5/00* (2006.01)
(Continued)

(52) U.S. Cl.
CPC ....... *A61M 25/0026* (2013.01); *A61B 5/6852* (2013.01); *A61M 1/32* (2013.01);
(Continued)

(58) Field of Classification Search
CPC .......... A61M 25/0026; A61M 25/0068; A61M 25/007; A61M 1/32; A61M 2025/1052; A61M 2205/3331; A61B 5/6852
See application file for complete search history.

(56) References Cited

U.S. PATENT DOCUMENTS 5,423,320 A * 6/1995 Salzman .................. A61B 5/42
600/473
9,919,276 B2 3/2018 Myrick et al.
(Continued)

FOREIGN PATENT DOCUMENTS

EP 1100560 B1 1/2008
JP 2002-521096 A 7/2002
(Continued)

OTHER PUBLICATIONS

EP Extended European Search Report in European Appln. No. 22757002.5, mailed on Dec. 4, 2024, 11 pages.
(Continued)

*Primary Examiner* — Tasnim Mehjabin Ahmed
(74) *Attorney, Agent, or Firm* — Fish & Richardson P.C.

(57) ABSTRACT

A catheter includes a catheter body, a first lumen extending through the catheter body, one or more second lumens extending through the catheter body, and two or more capillaries extending from the catheter body and coupled to the second lumens. The first lumen performs at least one of receiving a sample of the blood from a vasculature of the patient or measuring a parameter of the blood. The second lumens receive a gas enriched liquid from a gas enriched liquid source. The capillaries receive the gas enriched liquid
(Continued)

from the one or more second lumens and to simultaneously dispense respective streams of the gas enriched liquid directly into the vasculature, such that the streams of the gas enriched liquid intersect and mix with the blood in a region beyond an end of the catheter body and beyond the first lumen.

19 Claims, 13 Drawing Sheets

(51) Int. Cl.
*A61M 1/32* (2006.01)
*A61M 25/10* (2013.01)

(52) U.S. Cl.
CPC ....... *A61M 25/0068* (2013.01); *A61M 25/007* (2013.01); *A61M 2025/1052* (2013.01); *A61M 2202/0208* (2013.01); *A61M 2202/0216* (2013.01); *A61M 2202/0225* (2013.01); *A61M 2202/0266* (2013.01); *A61M 2202/0283* (2013.01); *A61M 2205/3331* (2013.01); *A61M 2230/00* (2013.01); *A61M 2230/205* (2013.01); *A61M 2230/30* (2013.01)

(56) References Cited

U.S. PATENT DOCUMENTS

2001/0001111 A1 5/2001 Spears
2006/0271093 A1 11/2006 Holman et al.
2009/0107503 A1 4/2009 Baran
2012/0302995 A1* 11/2012 Hochareon ..... A61M 1/362227 604/113
2013/0079859 A1* 3/2013 Dabrowiak ............... A61F 7/12 607/106
2018/0207592 A1* 7/2018 Myrick ............. B01F 25/31331

FOREIGN PATENT DOCUMENTS

JP 2013-518675 A 5/2013
JP 2014-527900 A 10/2014
JP 2020-533055 A 11/2020
WO WO 2013/165473 A1 11/2013

OTHER PUBLICATIONS

Creech et al., “Injection of highly supersaturated oxygen solutions without nucleation,” Journal of Biomechanical Engineering, Dec. 2002, 124(6):676-83.

Johnson et al., “Hyperbaric oxygen solution infused into the anterior interventricular vein at reperfusion reduces infarct size in swine,” American Journal of Physiology—Heart and Circulatory Physiology, Nov. 2004, 287(5):H2234-40.

PCT International Search Report and Written Opinion in International Appln. No. PCT/US2022/016988, dated Jul. 18, 2022, 13 pages.

* cited by examiner

CATHETERS AND SYSTEMS FOR DIRECT INJECTION OF GAS-ENRICHED LIQUID INTO A PATIENT

CLAIM OF PRIORITY

This application is the U.S. National Phase Application under U.S.C. § 371 of International Patent Application No. PCT/US2022/016988, filed on Feb. 18, 2022, which claims priority under 35 U.S.C. § 119(e) to U.S. provisional patent application Ser. No. 63/151,422, filed on Feb. 19, 2021, the entire contents of which are hereby incorporated by reference.

TECHNICAL FIELD

The disclosure relates to catheters and systems for injection of gas-enriched liquid into a patient.

BACKGROUND

Gas-enriched liquids are desirable in a wide variety of applications. However, at ambient pressure, the relatively low solubility of many gases, such as oxygen or nitrogen, within a liquid, such as water, produces a relatively low concentration of the dissolved gas in the liquid. One method of obtaining an increase in the gas concentration level without significant increase in liquid volume involves an injection and mixing of a gas-enriched liquid, such as a gas-supersaturated liquid, into a liquid of interest. A liquid can be gas enriched at high pressure.

Conventional methods for the delivery of oxygenated blood or oxygen-enriched liquids to tissues and bodily liquids involve the use of extracorporeal circuits for blood oxygenation. Extracorporeal circuits require withdrawing blood from a patient, circulating the blood through an oxygenator to increase blood oxygen concentration, and then delivering the blood back to the patient.

SUMMARY

In an aspect, a catheter is configured to be inserted into a vasculature of a patient. The catheter includes an elongated catheter body, a first lumen extending through the catheter body, one or more second lumens extending through the catheter body, and two or more capillaries extending from the catheter body and coupled to the one or more second lumens. The first lumen may be configured to be in fluid communication with the vasculature of the patient when the catheter is inserted into the vasculature of the patient, and the first lumen may be configured to perform at least one of receiving a sample of the patient's blood from the vasculature of the patient or measuring a parameter of the patient's blood. The one or more second lumens may be configured to receive a gas enriched liquid from a gas enriched liquid source. Each of the two or more capillaries are in fluid communication with the one or more second lumens and are configured to be in fluid communication with the vasculature of the patient when the catheter is inserted into the vasculature of the patient. Each of the two or more capillaries may be configured to receive the gas enriched liquid from the one or more second lumens and may be configured to simultaneously dispense respective streams of the gas enriched liquid directly into the vasculature of the patient.

The catheter body may be configured to position the two or more capillaries at one or more predetermined angles relative to one another, such that the streams of the gas enriched liquid intersect and mix with the patient's blood in a region beyond an end of the catheter body and beyond the first lumen. The first lumen may be recessed relative to respective output ends of the two or more capillaries. The first lumen may be recessed in a longitudinal or axial direction of the catheter body relative to respective output ends of the two or more capillaries. A capillary may also be referred to as a capillary tube, or just a tube. The first lumen may co-extend with the one or more second lumens. The first lumen may be in fluid isolation from the one or more second lumens within the body of the catheter.

Implementations of this aspect can include one or more of the following features.

In some implementations, the gas enriched liquid can be a supersaturated oxygen enriched liquid.

In some implementations, the first lumen can be configured to receive a guide wire for positioning the catheter with respect to the vasculature of the patient.

In some implementations, the catheter can further include a pressure sensor disposed within the first lumen. The pressure sensor can be configured to obtain one or more pressure measurements.

In some implementations, the parameter of the patient's blood can be at least one of a partial pressure of oxygen of the patient's blood, $SO_2$ of the patient's blood, a pressure of the patient's blood, a flow rate of the of the patient's blood, or a temperature of the of the patient's blood.

In some implementations, the first lumen can have a diameter ranging from 0.020 inches (about 0.5 mm) to 0.045 inches (about 1.1 mm).

In some implementations, the catheter can include a third lumen extending through the catheter body. The third lumen can be configured to be in fluid communication with the vasculature of the patient when the catheter is inserted into the vasculature of the patient. The third lumen can be configured to perform at least one of: receiving an additional sample of the patient's blood from the vasculature of the patient and measuring an additional parameter of the patient's blood.

In some implementations, the catheter body can be configured to position the two or more capillaries such that the streams of the gas enriched liquid intersect a longitudinal axis extending through a center of the catheter.

The catheter body can be configured to position the two or more capillaries. The two or more capillaries may be configured such that the streams of the gas enriched liquid intersect.

In some implementations, the catheter body can be configured to position the two or more capillaries such that the streams of the gas enriched liquid do not intersect a longitudinal axis extending through a center of the catheter.

In some implementations, the catheter can further include one or more shields or guards positioned over a distal opening of the first lumen and configured to reduce nucleation along one or more surfaces of the catheter.

In some implementations, at least one of the predetermined angles can range from 10 to 80 degrees.

In some implementations, a diameter of at least one of the two or more capillaries and a diameter of at least another one of the two or more capillaries can be equal.

In some implementations, a diameter of at least one of the two or more capillaries can be different from a diameter of at least another one of the two or more capillaries.

In some implementations, at least one of the two or more capillaries can have an inner diameter that ranges from 40 microns to 100 microns.

In some implementations, at least one of the two or more capillaries can have an outer diameter that ranges from 140 microns to 400 microns.

In some implementations, the two or more capillaries can include one or more elongated tubes extending from the catheter body.

In some implementations, a distance between (i) an intersection of the streams of the gas enriched liquid and (ii) an end tip of the catheter or an output aperture of the first lumen can be greater than or equal to a diameter of the end tip of the catheter.

In some implementations, a distance between (i) the output ends of the two or more capillaries and (ii) an end tip of the catheter or an output aperture of the first lumen can be greater than or equal to a diameter of the end tip of the catheter.

In some implementations, the at least one capillary can include a fiducial marking.

In some implementations, the streams of the gas enriched liquid can intersect and mix with the patient's blood without the formation of bubbles.

In some implementations, the streams of the gas enriched liquid can intersect and mix with the patient's blood in a region beyond an end of the catheter body and beyond the first lumen to reduce bubble nucleation along one or more surfaces of the catheter or capillaries.

In some implementations, the catheter can further include one or more sensors. The one or more sensors can be configured such that the one or more sensors are in fluid communication with the vasculature of the patient when the catheter is inserted into the vasculature of the patient.

In some implementations, at least one of the one or more sensors can be an oxygen partial pressure ($pO_2$) sensor.

In some implementations, the catheter can further include a self-centering device configured to center the catheter body within the vasculature of the patient.

In some implementations, the self-centering device can include one or more mesh structures encircling the catheter body.

In another aspect, a system can include a catheter as described herein, and a fluid dispensing device in fluid communication with the one or more second lumens. The fluid dispensing device can include one or more pumps configured to provide the gas enriched liquid to the one or more second lumens.

Implementations of this aspect can include one or more of the following features.

In some implementations, the system can include one or more connectors configured to couple the one or more second lumens to one or more respective dispensing ports of the fluid dispensing device.

In some implementations, at least one of the one or more connectors can be a high pressure Luer fitting.

In some implementations, the gas-enriched liquid can include one or more of oxygen, ozone, inert gas, nitrogen, nitrous oxide, carbon dioxide, or air.

In some implementations, the gas-enriched liquid can include a dissolved oxygen ($O_2$) concentration that ranges from 0.2 and 3 ml $O_2$/ml solvent.

In some implementations, the gas-enriched liquid can include a dissolved oxygen ($O_2$) concentration of 0.1-6 ml $O_2$/ml liquid (STP) or 0.2-3 ml $O_2$/ml liquid (STP).

In another aspect, a system includes a catheter as described herein, and a blood sampling device in fluid communication with the first lumen. The blood sampling device can be configured to withdraw the sample of the patient's blood from the vasculature of the patient through the first lumen.

Implementations of this aspect can include one or more of the following features.

In some implementations, the two or more capillaries can be coated with a hydrophilic coating.

As another aspect, a catheter is configured to be inserted into a vasculature of a patient. The catheter includes an elongated catheter body having a coiled shape, a first lumen extending through the catheter body, where the first lumen is configured to receive a gas enriched liquid, and a plurality of apertures positioned along a length of the catheter body. The plurality of apertures are in fluid communication with the first lumen. The apertures are configured to dispense the gas enriched liquid directly into the vasculature of the patient.

Implementations of this aspect can include one or more of the following features.

In some implementations, the gas enriched liquid can be a supersaturated oxygen enriched liquid.

In some implementations, the catheter can include one or more periodically repeating curved sections.

In some implementations, a length of each of the periodically repeating curved sections can vary.

In some implementations, the catheter body can have an inner diameter that ranges from 0.020 inches (about 0.5 mm) to 0.045 inches (about 1.1 mm).

In some implementations, the catheter body can have an outer diameter that ranges from 4 F to 12 F (about 1.33 mm to 4 mm).

In some implementations, the catheter can be at least partially composed of a shape-memory material.

In some implementations, one or more surfaces of the catheter can be composed of at least one of polycarbonate, glass, ceramic, stainless steel, polyether ether ketone (PEEK), or polyimide.

In some implementations, the catheter body can extend along an axial direction. At least some of the apertures can face one or more radial directions orthogonal to the axial direction.

In some implementations, each of the apertures can be positioned at a different respective radial position about the catheter body.

In some implementations, the catheter body can extend along an axial direction. Each of the apertures can face one or more radial directions orthogonal to the axial direction.

In some implementations, each of the apertures can have a diameter that ranges from 40 microns to 100 microns.

In some implementations, each of the apertures can have a circular shape.

In some implementations, the catheter body can extend along a helical path.

In some implementations, the catheter body can extend along a spiral path having a variable diameter.

In some implementations, adjacent apertures can be offset from one another along the catheter body by a distance that ranges from 1 cm to 5 cm.

In some implementations, the catheter body can be configured to receive a guiding rod.

In some implementations, the catheter body can be configured such that, when the guiding rod is inserted into the catheter body, a curvature of at least a portion of the catheter body is reduced.

In some implementations, the catheter can further include one or more elongated tubes extending from the catheter body. The one or more elongated tubes can include one or more second lumens in fluid communication with the apertures. The one or more elongated tubes can be configured to receive the gas enriched liquid from the apertures and to dispense the gas enriched liquid directly into the vasculature of the patient.

In some implementations, at least one of the one or more elongated tubes can branch into one or more respective portions, each defining a respective third lumen in fluid communication with the first lumen.

In some implementations, the gas-enriched liquid can include one or more of oxygen, ozone, inert gas, nitrogen, nitrous oxide, carbon dioxide, or air.

In some implementations, the gas-enriched liquid can include a dissolved oxygen ($O_2$) concentration that ranges from 0.2 to 3 ml $O_2$/ml solvent.

In some implementations, the gas-enriched liquid can include a dissolved oxygen ($O_2$) concentration of 0.1-6 ml $O_2$/ml liquid (STP) or 0.2-3 ml $O_2$/ml liquid (STP).

In another aspect, a system includes a catheter as described herein, and a fluid dispensing device in fluid communication with the first lumen. The fluid dispensing device includes one or more pumps configured to provide the gas enriched liquid to the first lumen.

Implementations of this aspect can include one or more of the following features.

In some implementations, the catheter can include a connector configured to couple the first lumen to a dispensing port of the fluid dispensing device.

In some implementations, the connector can be a Luer fitting.

In another aspect, a catheter is configured to be inserted into a vasculature of a patient. The catheter includes an elongated catheter body, a first lumen extending through the catheter body, where the first lumen is configured to receive a gas enriched liquid, and a plurality of elongated tubes extending along the catheter body. Adjacent elongated tubes can be offset from one another along the catheter body. Each of the elongated tubes includes a respective second lumen in fluid communication with the first lumen. The elongate tubes are configured to receive the gas enriched liquid from the first lumen and dispense the gas enriched liquid directly into the vasculature of the patient.

Implementations of this aspect can include one or more of the following features.

In some implementations, the gas enriched liquid can be a supersaturated oxygen enriched liquid.

In some implementations, at least one of the elongated tubes can branch into one or more respective portions.

In some implementations, each of the portions can be in fluid communication with the first lumen.

In some implementations, each of the portions can include a respective output end. Each of the output ends can be positioned at a different respective radial position about the catheter body.

In some implementations, the catheter body can have an inner diameter that ranges from 0.020 inches (about 0.5 mm) to 0.045 inches (about 1.1 mm).

In some implementations, the catheter body can have an outer diameter that ranges from 4 F to 12 F (about 1.33 mm to 4 mm).

In some implementations, at least one of the elongated tubes can have an inner diameter that ranges from 40 microns to 100 microns.

In some implementations, at least one of the elongated tubes can have an outer diameter that ranges from 140 microns to 400 microns.

In some implementations, at least one of the elongated tubes can have a circular cross-section.

In some implementations, the adjacent elongated tubes can vary in length from one another by a length that ranges from 1 cm to 5 cm.

In some implementations, the adjacent elongated tubes can be offset from one another along the catheter body by a distance that ranges from 1 cm to 5 cm.

In some implementations, the gas-enriched liquid can include one or more of oxygen, ozone, inert gas, nitrogen, nitrous oxide, carbon dioxide, or air.

In some implementations, the gas-enriched liquid can include a dissolved oxygen ($O_2$) concentration that ranges from 0.2 to 3 ml $O_2$/ml solvent.

In some implementations, the gas-enriched liquid can include a dissolved oxygen ($O_2$) concentration of 0.1-6 ml $O_2$/ml liquid (STP) or 0.2-3 ml $O_2$/ml liquid (STP).

In some implementations, the at least one capillary can include a fiducial marking.

In some implementations, the catheter can be sufficiently flexible to be guided through a catheter delivery system.

In another aspect, a system includes a catheter as described above, and a fluid dispensing device in fluid communication with the first lumen. The fluid dispensing device can include one or more pumps configured to provide the gas enriched liquid to the first lumen.

In some implementations, the catheter can include a connector configured to couple the first lumen to a dispensing port of the fluid dispensing device.

In some implementations, the connector can be a Luer fitting.

In general, an implementation described with respect to one aspect may be provided in combination with another aspect. The details of one or more embodiments are set forth in the accompanying drawings and the description. Other features and advantages will be apparent from the description and drawings, and from the claims.

DETAILED DESCRIPTION

Figure 1A:
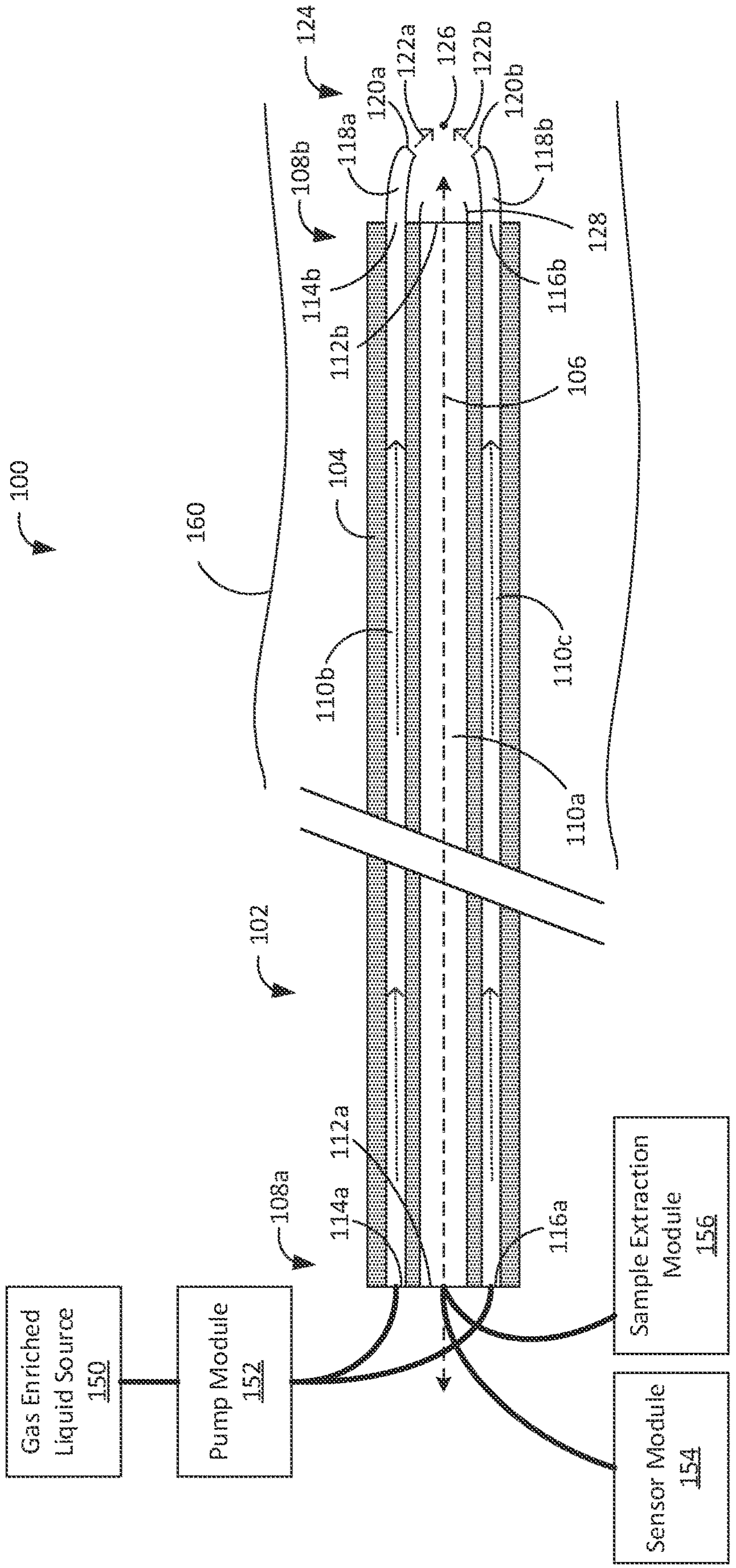
FIGS. 1A and 1B are diagrams of an example system for enriching a bodily liquid with a gas-enriched liquid inside of an enclosed area of a body.

FIG. 1A shows an example system 100 for enriching a bodily liquid with a dissolved gas or gas enriched liquid inside of an enclosed area of a body. As an example, the system 100 can be used to enrich a patient's blood with supersaturated oxygen enriched liquid or supersaturated liquid within the vasculature of the patient thereby delivering supersaturated oxygen ($SSO_2$) therapy to a patient, increasing oxygen in the blood and diffusion of oxygen into tissue. In certain implementations, oxygen enriched liquid or solution, e.g., supersaturated oxygen enriched liquid or solution, may include liquid having a dissolved $O_2$ concentration of 0.1 ml $O_2$/ml liquid (STP) or greater or 0.1-6 ml $O_2$/ml liquid (STP) or 0.2-3 ml $O_2$/ml liquid (STP) (e.g., without clinically significant gas emboli).

As shown in FIG. 1A, the system 100 includes a catheter 102, a gas enriched liquid source 150, a pump 152, a sensor 154, and a sample extraction device 156. The catheter 102 is configured to be inserted into the vasculature of a patient, to facilitate the delivery of a gas enriched liquid (e.g., from the gas enriched liquid source 150) into the vasculature of the patient via the pump 152. Further, the catheter 102 is configured to facilitate the measurement of one or more properties of the patient's blood within the patient's vasculature (e.g., by providing the sensor 154 access to the patient's vasculature) and/or to facilitate the collection of blood samples from the patient's vasculature (e.g., by providing the sample extraction device 156 access to the patient's vasculature). For example, the sensor 154 may positioned on the distal (or first) end 108*a* of the catheter 102 or in a communicating lumen of the catheter 102. The sensor 154 can detect various blood parameters (e.g., partial pressure of oxygen in the patient's blood ($pO_2$), the oxygen saturation of the patient's blood ($SO_2$), the flow rate of the patient's blood, a temperature of the patient's blood), during treatment or after treatment is paused or completed.

The catheter 102 includes an elongated catheter body 104 (e.g., extending along a longitudinal axis 106 through the center of the catheter body 104) having a proximal (or second) end 108*b* opposing the distal end 108*a*. In some implementations, the catheter can have a circular, elliptical, or ovular cross-section along a portion of or an entirety of its length. In some implementations, the catheter body 104 can be flexible (e.g., such that it can be bent or curved at one or more locations along its length. In some implementations, at least a portion of the catheter 102 and/or the catheter body 104 can be composed of polycarbonate, glass, ceramic, stainless steel, polyether ether ketone (PEEK), polyether block amide (PEBA) (e.g., PEBAX produced by Akrema S.A., Colombes, France), acrylonitrile butadiene styrene (ABS), polyimide, and/or other suitable materials. In some implementations, the catheter body 104 can have an outer diameter ranging from 4 F to 12 F, or for example, 4 F to 6 F (according to the French scale—about 1.33 mm to 4 mm or about 1.33 mm to 2 mm).

Further, the catheter 102 includes multiple lumens extending through the catheter body 104. In this example, the catheter 102 includes one or more communicating lumens 110*a* extending through a center of the catheter body 104 (e.g., along the longitudinal axis 106). At least two additional lumens 110*b* and 110*c* may extend through opposing sides of the catheter body 104 (e.g., parallel to the communicating lumen 110*a*). Each of the lumens 110*a*-110*c* can have a circular, elliptical, or ovular cross-section along a portion of or an entirety of its length. In some implementations, the communicating lumen 110*a* can have an inner diameter ranging from 0.020 inches to 0.045 inches (about 0.5 mm to about 1.1 mm).

Each of the lumens 110*a*-110*c* includes a respective input aperture and a respective output aperture. For example, the communicating lumen 110*a* includes an input aperture 112*a* on the first (or distal) end 108*a* of the catheter body 104 and an output aperture 112*b* on the second (or proximal) end 108*b* of the catheter body 104. As another example, the lumen 110*b* includes an input aperture 114*a* on the first end 108*a* of the catheter body 104 and an output aperture 114*b* on the second end 108*b* of the catheter body 104. As another example, the lumen 110*c* includes an input aperture 116*a* on the first end 108*a* of the catheter body 104 and an output aperture 116*b* on the second end 108*b* of the catheter body 104.

Further, the catheter 102 includes a capillary 118*a* extending from and in fluid communication with the output aperture 114*b* of the lumen 110*b* (e.g., such that fluid can flow from the lumen 110*b* into the capillary 118*a*. The capillary 118*a* terminates at an output aperture 120*a*. In some implementations, the capillary 118*a* can have an inner diameter between 40 microns and 100 microns. In some implementations, the capillary 118*a* can have an outer diameter between 140 microns and 160 microns. In some implementations, the capillary 118*a* can have a length ranging from 5 cm to 10 cm or be a length "I" which is substantially equal to the diameter of the catheter tip or distal end.

The catheter 102 also includes a capillary 118*b* extending from and in fluid communication with the output aperture 116*b* of the lumen 110*c* (e.g, such that fluid can flow from the lumen 110*c* into the capillary 118*b*. The capillary 118*b* terminates at an output aperture 120*b*. In some implementations, the capillary 118*b* can have an inner diameter from 40 microns to 100 microns. In some implementations, the capillary 118*b* can have an outer diameter from 140 microns to 400 microns. In some implementations, the capillary 118*b* can have a length ranging from 5 cm to 10 cm or be a length "I" which is substantially equal to the diameter of the catheter tip or distal end.

In some implementations, the capillaries 118*a* and 118*b* may have identical or different sized inner and/or outer diameters. In some implementations, the capillaries 118*a* and 118*b* may have identical or different sized lengths.

During an example usage of the system 100, the gas enriched liquid source 150 and the pump 152 are coupled to the catheter 102, such that the gas enriched liquid source 150 and the pump 152 are in fluid communication with the input apertures 114*a* and 116*a* of the lumens 110*b* and 110*c*, respectively. As an example, one or more fluid-tight tubes can be used to convey gas enriched liquid from the gas enriched liquid source 150 to the pump 152, and from the pump 152 to the input apertures 114*a* and 116*b*. In some implementations, one or more fluid-tight tubes can be used to convey gas enriched liquid from the gas enriched liquid source 150 to the input apertures 114*a* and 116*b*, where at least a portion of the one or more fluid-tight tubes are coupled to a peristaltic pump or form part of the peristaltic pump, which urges fluid from the gas enriched liquid source to the input apertures 114*a* and 116*b*. In some implementations, the tubes can be secured to the input apertures 114*a* and 116*b* using a fitting or connector, such as a high-pressure Luer fitting.

In some implementations, the gas enriched liquid source 150 can include one or more storage tanks for storing the gas enriched liquid. In some implementations, the gas enriched liquid can be a supersaturated oxygen enriched liquid or supersaturated liquid, such as a liquid having a dissolved oxygen ($O_2$) concentration between 0.2 and 3 ml $O_2$/ml solvent (which is the concentration equivalent of 100 psi to 1500 psi). In some implementations, the gas enriched liquid can include liquid enriched with oxygen, ozone, inert gas, nitrogen, nitrous oxide, carbon dioxide, and/or air. In some implementations, the gas enriched liquid source 150 may include an oxygenation device, which is operated by a console or hardware component that controls operation of the oxygenation device, as described in U.S. Pat. No. 9,919,276, the entire disclosure of such patent being expressly incorporated herein by reference in its entirety. The console or hardware component may include a controller, processor, memory and associated circuitry. The oxygenation device may include a fluid supply chamber for receiving a physiologic liquid e.g., saline from an IV bag, and an atomization chamber for receiving a suitable gas, e.g., oxygen from an oxygen tank. The saline is pumped into the oxygen-pressurized atomization chamber and atomized to create gas-enriched or supersaturated liquid, e.g., supersaturated oxygen-enriched saline or supersaturated saline. In certain implementations, the gas-enriched liquid can be oxygen enriched liquid or solution, e.g., supersaturated oxygen enriched liquid or solution, may include liquid having a dissolved ($O_2$) concentration of 0.1 ml $O_2$/ml liquid (STP) or greater or 0.1-6 ml $O_2$/ml liquid (STP) or 0.2-3 ml $O_2$/ml liquid (STP) (e.g., without clinically significant gas emboli). In some implementations, the gas enriched liquid can be a supersaturated oxygen enriched liquid or solution (e.g., saline with a dissolved (2 concentration in saline of 0.1 ml $O_2$/ml saline (STP) or greater or 0.1-6 ml $O_2$/ml saline (STP) or 0.2-3 ml $O_2$/ml saline (STP) (e.g., without clinically significant gas emboli).

Further, a portion of the catheter 102 is inserted into a patient, such as the second end 108*b* of the catheter body 104 is positioned within a vasculature of a patient (e.g., a blood vessel 160, such as a vein or artery). After the catheter 102 has been inserted into the patient, the pump 152 is activated, such that it draws the gas enriched liquid from the gas enriched liquid source 150, and pumps the gas enriched liquid, e.g., supersaturated liquid, into each of the lumens 110*b* and 110*c*. The gas enriched liquid flows through the lumens 110*b* and 110*c* and into the capillaries 118*a* and 118*b* and is expelled from the output apertures 120*a* and 120*b* as two respective streams 122*a* and 122*b*.

In some implementations, the system 100 can be configured to expel streams according to different flow rates and/or pressures. For example, the system 100 can be configured to expel streams between 1 mL/minute (e.g., at a pressure of 100 psi, about 690 kPa) to 3 mL/minute (e.g., at a pressure of 300 psi, about 2 MPa).

The capillaries 118*a* and 118*b* are configured such that the streams 122*a* and 122*b* intersect with one another and mix in a mixing region 124 within the vasculature of the patient. For example, the capillaries 118*a* and 118*b* can define respective paths that are angled relative to the longitudinal axis 106, such that the streams 122*a* and 122*b* are expelled from the output apertures 120*a* and 120*b* at respective angles relative to the longitudinal axis 106. In some implementations, the capillaries 120*a* and 120*b* can be configured such that the streams 122*a* and 122*b* intersect at a point 126 beyond the tip of the catheter 102 (e.g., where the point 126 is on or around the longitudinal axis 106). For example, the streams 122*a* and 122*b* may mix without bubble formation or without significant bubble formation in the mixing region 124 at a distance downstream from the output apertures of the capillaries 118*a* and 118*b*.

Further, the communicating lumen 110*a* provides access to the vasculature of the patient. For example, in some implementations, a sensor 154 can be at least partially inserted into the communicating lumen 110*a*, such that it is in fluid communication with the blood of the patient. In other implementations, the sensor may be located outside of the communicating lumen or on a catheter wall. The sensor 154 can obtain one or more sensor measurements regarding the blood and provide feedback regarding measured parameters affected by the $SSO_2$ therapy in order to optimize the $SSO_2$ therapy. For example, the sensor 154 can measure a partial pressure of oxygen of the patient's blood, an oxygen concentration or $SO_2$ of the patient's blood, a pressure of the patient's blood, e.g., arterial blood pressure, a flow rate of the of the patient's blood, and/or a temperature of the of the patient's blood.

Examples of such sensors include the following:

One example of a sensor for measuring a partial pressure ($pO_2$) of oxygen or oxygen saturation $SO_2$ in the patient's blood is a pulse oximeter. A pulse oximeter may be used for estimating arterial $pO_2$ or $SO_2$. Pulse oximetry estimates the percentage of oxygen bound to hemoglobin in the blood. A pulse oximeter uses light-emitting diodes and a light-sensitive sensor to measure the absorption of red and infrared light. In another example, a sensor for measuring partial pressure of oxygen comprises an electrode such as a Clark electrode for measuring $pO_2$. A Clark electrode is an electrode that measures ambient oxygen concentration in a liquid using a catalytic platinum surface according to the net reaction O2+4 e−+4 H+→2 H2O. The various sensors may be coupled to a controller of the system via a cable or other wired connection or via a wireless connection.

The processor can receive the signals from these sensors, which signals correspond to the measured values of $pO_2$. The processor compares the measured $pO_2$ to a target range of blood $pO_2$, e.g., 760-1500 mmHg (about 100 kPa to 200 kPa). The target range may be calculated based on a blood flow rate of 50-150 ml/min, saline flow rate of 2-5 ml/min and dissolved $O_2$ concentration in saline of 0.2-3 ml $O_2$/ml saline (STP). The controller can adjust the saline flow rate and/or dissolved $O_2$ concentration in saline based on the measured $pO_2$ in blood to achieve an arterial blood $pO_2$ within the target range. The processor may generate an alert, e.g., through a user interface, audible alarm and/or visual alarm that indicates the level of $pO_2$. The measured $pO_2$ indicates the effectiveness of the supersaturated oxygen therapy, letting the caregiver know if the $pO_2$ in blood is within the target range for optimizing the delivery of oxygen to the patient's ischemic tissue. In certain implementations, the processor may control the delivery of supersaturated oxygen therapy by modifying one or more of the above referenced saline or oxygen parameters based on the signals received from the sensors.

Another example of a sensor is an $O_2$ fluorescence probe. The fluorescence probe may be coupled to a controller of the system via a cable or other wired or wireless connection. A light source of the $O_2$ fluorescence probe is illuminated. A fiber optic cable can be used to provide light to the light source in certain implementations, where the fiber optic cable is connected to the controller of the system. The fluorescence of a sensor molecule of the $O_2$ fluorescence probe is measured. The sensor molecule can include fluorophore. A signal is received by the processor from the $O_2$ fluorescence probe based on the fluorescence measurement. Fluorescence is measured by measuring the lifetime or decay of the fluorescence intensity signal from the illuminated sensor molecule (e.g., fluorophore) on the fluorescence probe. The decay of this signal is caused by the quenching effect of oxygen molecules in the blood or in tissue on the fluorescence intensity signal of the sensor molecule. The processor can determine the oxygen concentration, $SO_2$ or $pO_2$ in blood or tissue based on the quenching effect of oxygen on the florescence intensity signal of the florescence probe. Changes in the amount of time that is required for the signal to decay due to oxygen quenching are indicative of the local oxygen concentration, $SO_2$ or $pO_2$ in blood or tissue. The processor generates an alert, e.g., through a user interface, audible alarm and/or visual alarm, based on the determined oxygen concentration, $SO_2$ or $pO_2$ in blood or tissue. The alert may indicate the effectiveness of the supersaturated oxygen therapy. The determined oxygen concentration, $SO_2$ or $pO_2$ indicates the effectiveness of the supersaturated oxygen therapy, letting the caregiver know if the oxygen concentration, $SO_2$ or $pO_2$ in blood is within a predefined target range (e.g., the expected range for a healthy individual) for optimizing the delivery of oxygen to the patient. In certain implementations, the processor may control the delivery of supersaturated oxygen therapy by modifying one or more of the saline or oxygen parameters, e.g., saline flow rate or dissolved $O_2$ concentration in saline, based on the determined oxygen concentration, $SO_2$ or $pO_2$ values.

Another example of a sensor is a temperature sensor located on or in the catheter. For example, a thermistor may be utilized to measure the blood temperature of the patient. The processor can receive signals from the thermistor, which signals correspond to the measured values of the blood temperature. The processor may generate an alert, e.g., through a user interface, audible alarm and/or visual alarm that indicates the blood temperature, which may alert the caregiver of a hypothermic or hyperthermic, e.g., febrile, state of the patient.

An example sensor for measuring an arterial pressure of the patient's blood would be a pressure sensor positioned in or coupled to the communicating lumen. The communicating lumen may be used for direct measurement of arterial pressure. The communicating lumen may be connected to a fluid-filled system, which is connected to an electronic pressure transducer. A change in detected blood pressure may be indicative of improved perfusion and/or restored flow in ischemic tissue as a result of the $SSO_2$ therapy. The therapy may result in improved heart function. In certain implementations, the processor may control the delivery of supersaturated oxygen therapy based on the arterial pressure feedback.

An example sensor used to determine a blood flow rate includes a temperature sensor, e.g., a thermistor, thermocouple or thermal anemometer. A temperature sensor may be located on a catheter tip, capillary tip or in the communication lumen. The temperature sensor may be heated, such that the sensor temperature is raised. As blood flows past the temperature sensor, the degree to which the temperature sensor cools down is indicative of the flow rate past the temperature sensor. The determined blood flow rate may be fed back to the system and may be indicative of the efficacy of the $SSO_2$ therapy, which results in improved perfusion and/or restored flow in ischemic tissue. In certain implementations, the processor may control the delivery of supersaturated oxygen therapy based on the blood flow rate feedback.

If the sensor is a pressure sensor, the sensor may detect a pressure differential between ambient pressure and arterial pressure or an absolute value of arterial pressure. The pressure sensor may be placed anywhere in the communicating lumen but does not necessarily have to be positioned in the communicating lumen, and can be located outside of the lumen. One example of a pressure sensor is a strain gauge. In a catheter having multiple communicating lumens, a pressure sensor may be located in a first communicating lumen providing an uninterrupted pressure signal while blood sampling may be performed via a second communicating lumen simultaneously. In another example, two pressure sensors can be used, with one located in a first communicating lumen and one located in a second communicating lumen to provide redundancy of pressure readings.

As another example, in some implementations, a sample extraction device 156 can be used to obtain a sample of the patient's blood via the communicating lumen 110*a*. For example, the sample extraction device 156 can include one or more pumps or syringes to draw a sample of the patient's blood through the lumen 110*a* and out of the patient's body. The syringe may be coupled to a proximal end of the catheter for sampling. A valve or stopcock may be included at the proximal end of one more lumen of the catheter to control sampling.

In some implementation, the communicating lumen 110*a* can also be used to guide the catheter 102 within the patient's body. For example, a guide wire can be inserted into the communicating lumen 110*a*, and manipulated to control the shape and/or position of the catheter 102 within the patient's body.

Further, the catheter 102 may be configured in such a way that eliminates or otherwise reduces the formation of bubbles within the vasculature of the patient. For example, the streams 122*a* and 122*b* mix in a mixing region 124 away from any surfaces of the catheter 102 or capillaries thereby reducing, preventing or reducing the likelihood of bubble formation through nucleation on the surfaces of the catheter 102 or capillaries.

Figure 1B:
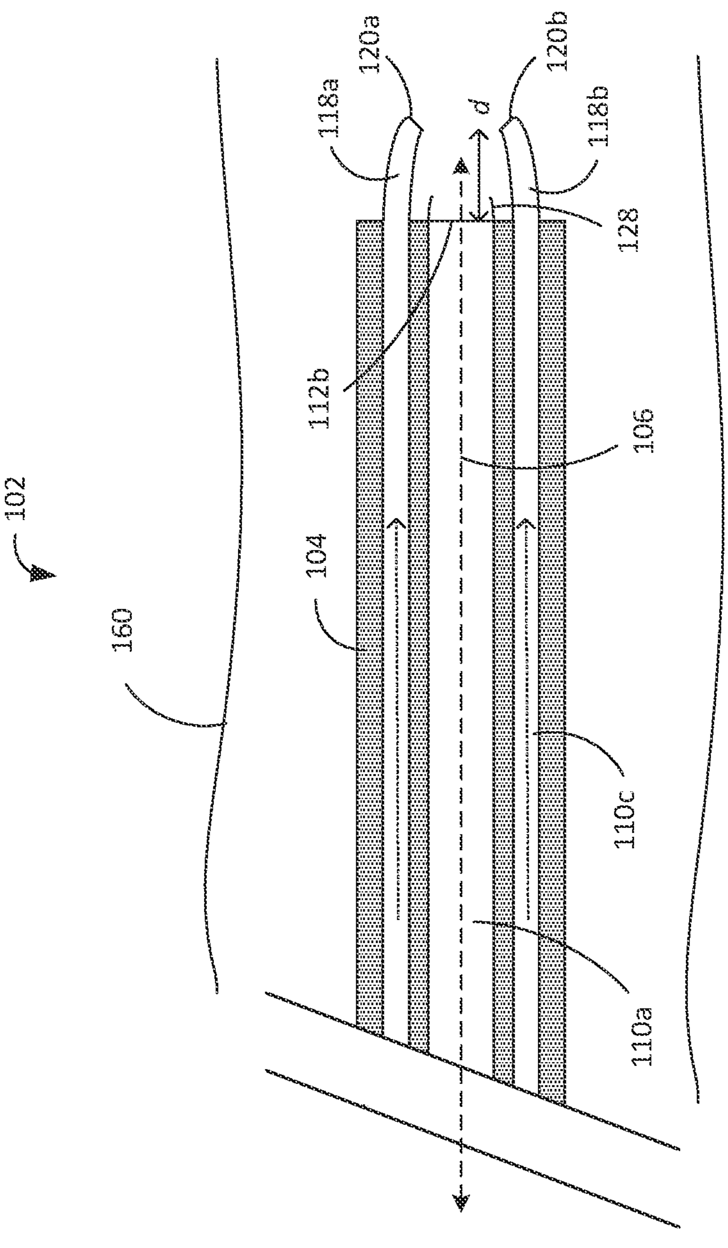

Further, as shown in FIG. 1B, the output aperture 112*b* of the communicating lumen 110*a* is recessed from the output apertures 120*a* and 120*b* of the capillaries 118*a* and 118*b* (e.g., by a distance d along a direction of the longitudinal axis 106). Accordingly, the streams 122*a* and 122*b* are less likely to impinge on the surfaces of the lumen 110*a*, thereby further preventing or reducing the likelihood of bubble formation through nucleation. Further, the streams 122*a* and 122*b* are less likely to interfere with the obtaining of sensor measurements by the sensor 154. In some implementations, the distance d can be selected based on the dimensions of the tip of the catheter 102. For example, the distance d can be at least as long as the diameter of the tip or distal end of the catheter 102. In some implementations, the distance d can be 0.060 inches (about 1.5 mm) to 0.100 inches (about 2.5 mm). As shown in FIGS. 1A and 1B, in some implementations, the catheter 102 can also include one or more shields or guards 128 (e.g., protrusions, walls, bumps, etc.) positioned over the output aperture 112*b* to reduce nucleation along one or more surfaces of the catheter.

In certain examples, d is scaled to the diameter of the catheter. The diameter of the catheter tip or distal end will vary depending on factors such as artery size, blood flow rate, and blood back flow. The mixing region, where the streams intersect, may create a mixing zone away from the catheter distal end. Because the diameter of catheter tip will affect blood flow and turbulence in that mixing zone, it is important to ensure that the mixing zone is at least a distance d from the catheter tip and the output aperture of the communicating lumen. In certain examples, a distance d that is substantially equal to the diameter of the catheter tip is the minimum distance that the mixing zone should be located from the catheter tip. This helps avoid the effects of the catheter tip diameter on mixing. A recessed output aperture of the communicating lumen also helps ensure the reliability of blood samples removed via the communicating lumen. It is desirable for the mixing zone to be at least a distance d away from the output aperture of the communicating lumen, to avoid sampling of unmixed $SSO_2$ solution. Also, when detecting pressure, a sufficiently recessed output aperture of a communicating lumen results a reduction in noise in the pressure measurement. In some implementations, the distance d can be 0.060 inches (about 1.5 mm) to 0.100 inches (about 2.5 mm).

Further, each of the surfaces of the catheter 102 (e.g., the interior surfaces of the lumens 110*a*-110*c* and the capillaries 118*a* and 118*b*, the exterior surfaces of the capillaries 118*a* and 118*b*, the exterior surfaces of the catheter body 104, etc.) can be smooth to prevent or further reduce the likelihood of bubble formation through nucleation. In some implementations, one or more of these surfaces can be coated or pre-wetted with liquids and/or hydrophilic agents or coatings (e.g., saline, ethanol, benzalkonium heparin, blood proteins, etc.) before use to further inhibit the formation of bubbles through nucleation.

Figure 2B:
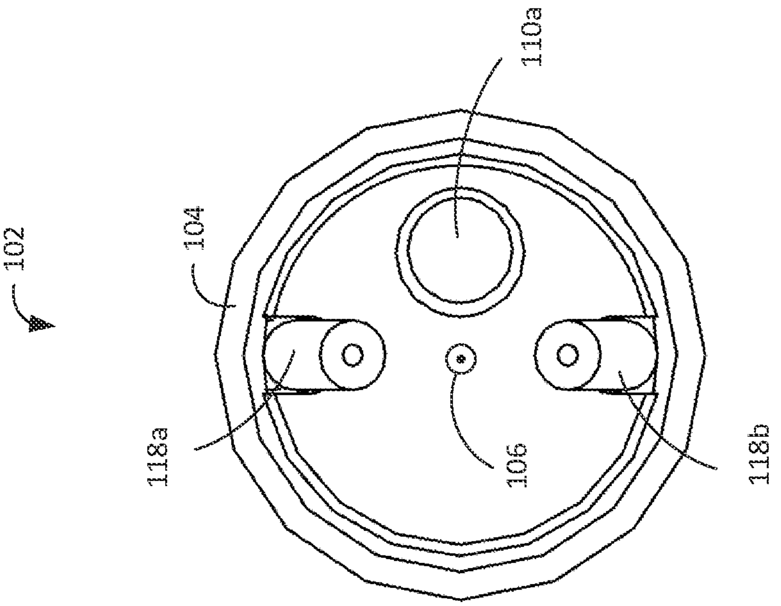
FIGS. 2A and 2B are diagrams of an example catheter.
Figure 2A:
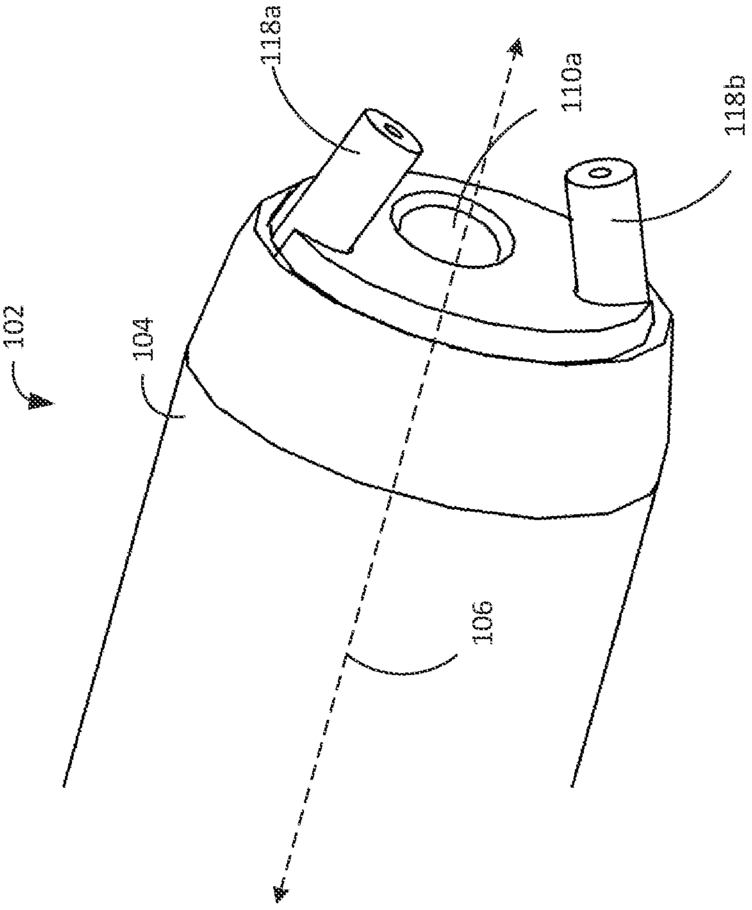

In the example shown in FIGS. 1A and 1B, the lumen 110*a* extends along a longitudinal axis 106 through a center of the catheter body 104. However, this need not always be the case. For instance, FIGS. 2A and 2B show a perspective view and a head-on view, respectively, of another example catheter 102. In this example, the lumen 110*a* is positioned off-center along the catheter body 104, such that it extends parallel to the longitudinal axis (rather than along the longitudinal axis 106).

Figure 3B:
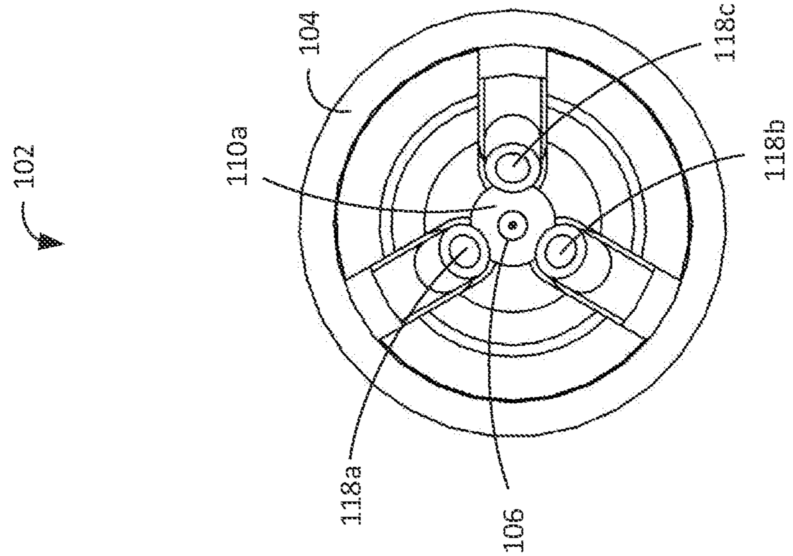
FIGS. 3A and 3B are diagrams of another example catheter.
Figure 3A:
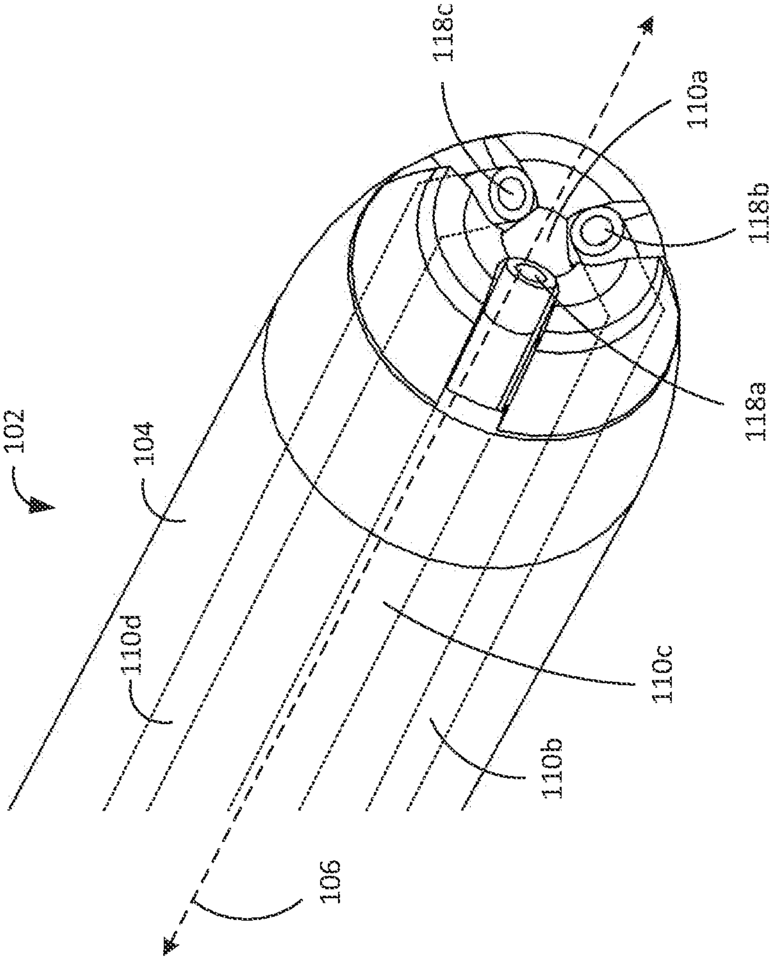

Further, in the example shown in FIGS. 1A and 1B, the catheter 102 includes two lumen 110*b* and 110*c* and two capillaries 118*a* and 118*b* for conveying a gas enriched liquid into the vasculature of a patient. However, this also need not always be the case. For instance, FIGS. 3A and 3B show a perspective view and a head-on view, respectively, of another example catheter 102. In this example, the catheter 102 includes three lumen 110*b*-110*d* extending through the catheter body 104, each configured to convey a gas enriched liquid into the vasculature of a patient. Further, the catheter 102 includes three capillaries 118*a*-118*c* extending from and in fluid communication with the lumens 110*b*-110*d*, respectively. During an example usage of the system 100, the gas enriched liquid source 150 and the pump 152 are attached to the catheter 102, such that the gas enriched liquid source 150 and the pump 152 are in fluid communication with the input apertures of each of the lumens 110*b*-110*d*. Further, the pump 152 is activated, such that it draws a gas enriched liquid from the gas enriched liquid source 150, and pumps the gas enriched liquid into each of the lumens 110*b*-110*d*. The gas enriched liquid flows through the lumens 110*b*-110*d* and into the capillaries 118*a*-118*c*, and is expelled from the capillaries 118*a*-118*c* as three respective streams.

Further, the capillaries 118*a*-118*c* are configured such that the streams mix in a mixing region within the vasculature of the patient. For example, the capillaries 118*a*-118*c* can define respective paths that are angled relative to the longitudinal axis 106, such that the streams are expelled from the capillaries 118*a*-118*c* at respective angles relative to the longitudinal axis 106. In some implementations, the capillaries 118*a*-118*c* can be configured such that at least two of the streams intersect at a point some distance beyond the tip of the catheter 102. In some implementations, the capillaries 118*a*-118*c* can be configured such all of the streams intersect at a point some distance beyond the tip of the catheter 102 (e.g., a point on the longitudinal axis 106).

Although FIGS. 3A and 3B show an example catheter having three lumens and three capillaries for conveying a gas enriched liquid, this is merely an illustrative example. In practice, a catheter can have any number of lumen and capillaries for conveying a gas enriched liquid. As an example, a catheter can include one, two, three, four, or more lumens for conveying a gas enriched liquid. As another example, a catheter can include one, two, three, four, or more capillaries for conveying a gas enriched liquid.

In some implementations, a catheter may have a plurality of lumens coupled to a plurality of capillaries. For example, while not shown in the figures, the catheter may include a single capillary and a plurality of lumens, where certain of the plurality of lumens may converge and be coupled to the single capillary and other of the plurality of lumens may serve as communicating lumens for performing at least one of receiving a sample of a patient's blood from the vasculature of the patient or measuring a parameter of the patient's blood. The stream may exit the output aperture of the single capillary without intersecting a vessel wall and mix with the blood without bubble formation at a distance downstream from the output aperture of the capillary. A single capillary catheter may also be utilized for indications where bubble formation is less of a concern, e.g., where blood flow is not going to the heart or brain, but instead is being pushed to a capillary bed or patient tissue, or when targeting venous blood flow.

Further, although the example catheters described above each have a single lumen for facilitating the measurement of one or more properties of the patient's blood within the patient's vasculature and/or facilitating the collection of blood samples from the patient's vasculature, this need not always be the case. In practice, a catheter can have any number of lumen for facilitating the measurement of one or more properties of the patient's blood within the patient's vasculature and/or facilitating the collection of blood samples from the patient's vasculature (e.g., one, two, three, four, or more).

Figure 4B:
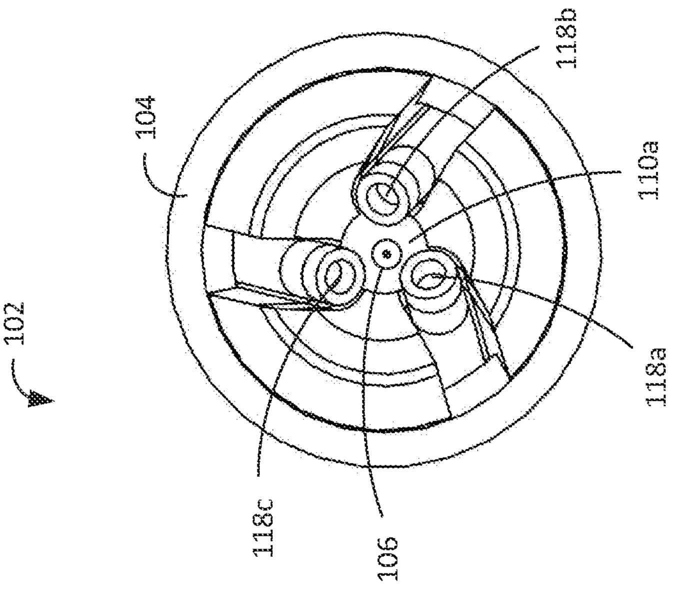
FIGS. 4A and 4B are diagrams of another example catheter.
Figure 4A:
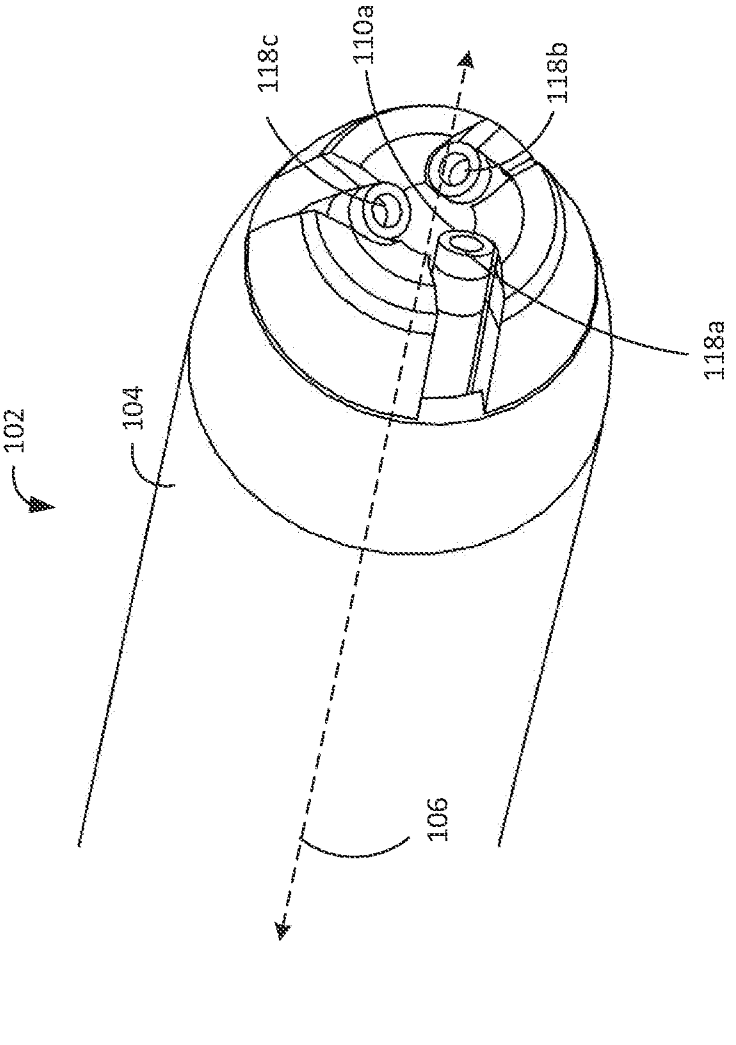

As shown in FIGS. 3A-3C, the capillaries 118*a*-118*c* can be configured such that all or two or more of the streams expelled by the capillaries 118*a*-118*c* intersect at a point along the longitudinal axis 106, beyond the tip of the catheter 102. For example, as shown in FIG. 3B, in cross-section, each of the capillaries 118*a*-118*c* can extend radially from the longitudinal axis 106. However, this also need not always be the case. For instance, FIGS. 4A and 4B show a perspective view and a head-on view, respectively, of another example catheter 102. In this example, in cross-section, each of the capillaries 118*a*-118*c* does not extend radially from the longitudinal axis 106. Instead, in cross section, each of the capillaries 118*a*-118*c* is offset relative to a respective radius by a particular angle, such that the streams expelled by the capillaries 118*a*-118*c* interact at points that are not on the longitudinal axis 106. This can be beneficial, for example, in facilitating the mixing of the gas enriched liquid with the patient's blood in a spiral or vortex pattern, which may further suppress, reduce, or prevent the formation of bubbles. Having angled capillaries may create angular momentum, which causes rotational mixing. This may result in improved overall mixing. In certain examples, the capillaries may be offset or angled relative to each other at an angle ranging from greater than 0 degrees to 15 degrees. In general, reference to an axial direction of the catheter may be considered to be a longitudinal direction of the catheter. Further, reference to a radial direction of the catheter may be considered to be a lateral direction of the catheter.

Figure 5A:
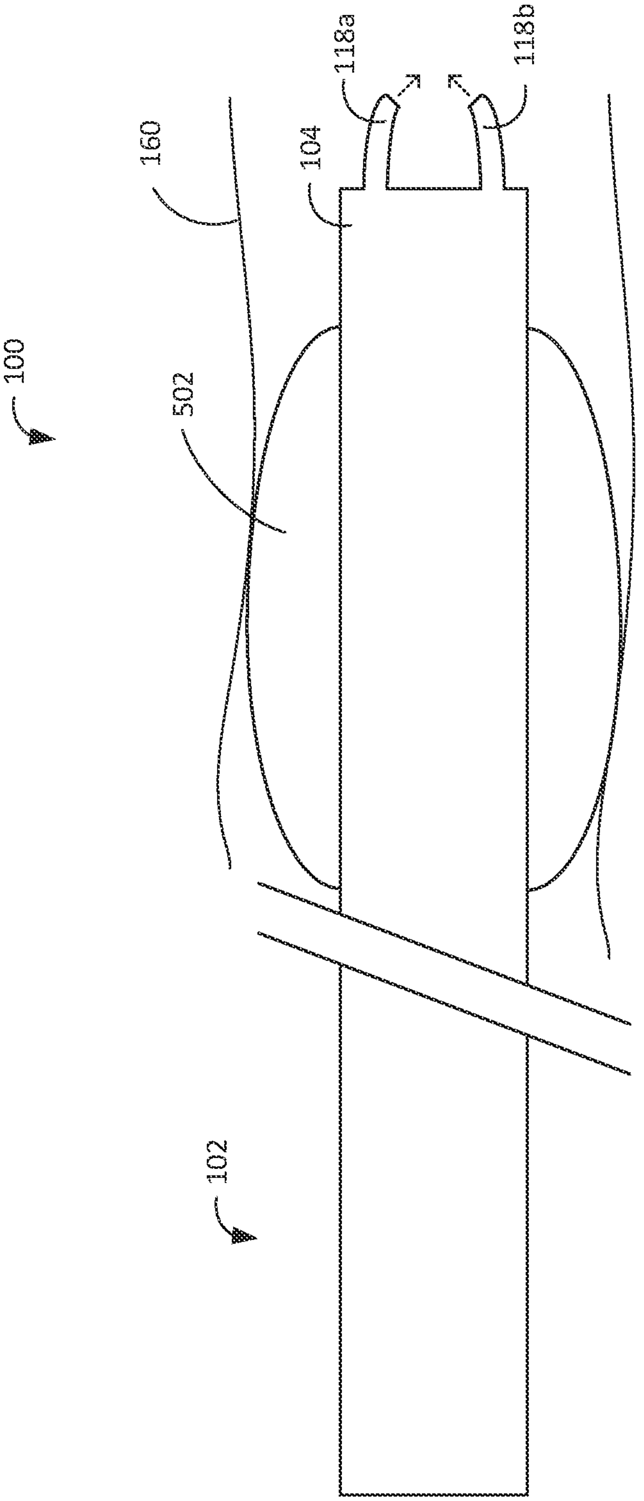
FIG. 5A is a diagram of an example catheter including an inflatable balloon structure.

In some implementations, the system 100 can also include self-centering mechanisms for positioning the catheter 102 within the vasculature of the patient (e.g., such that the catheter body 104 capillaries and/or the streams expelled by the capillaries are positioned centrally in a vein or artery, away from the vessel walls to reduce or prevent nucleation or bubble formation by preventing the streams from hitting a vessel wall). For instance, FIG. 5A shows an example catheter 102 including an inflatable balloon structure 502. The balloon structure 502 encircles a portion of the catheter 104, and can be selectively inflated and deflated. For example, after a portion of the catheter 102 has been inserted into a vessel 160, the balloon structure 502 can be inflated such that it contacts the walls of the vessel 160. In this configuration, the catheter 104 body is positioned centrally within the vessel 160. Accordingly, the streams of gas enriched liquid expelled by the capillaries 118*a* and 118*b* mix in a mixing region away from the walls of the vessel 160. This can be beneficial, for example, in reducing mechanical stress on the walls of the vessel and in further suppressing, preventing, or reducing the formation of bubbles.

Figure 5B:
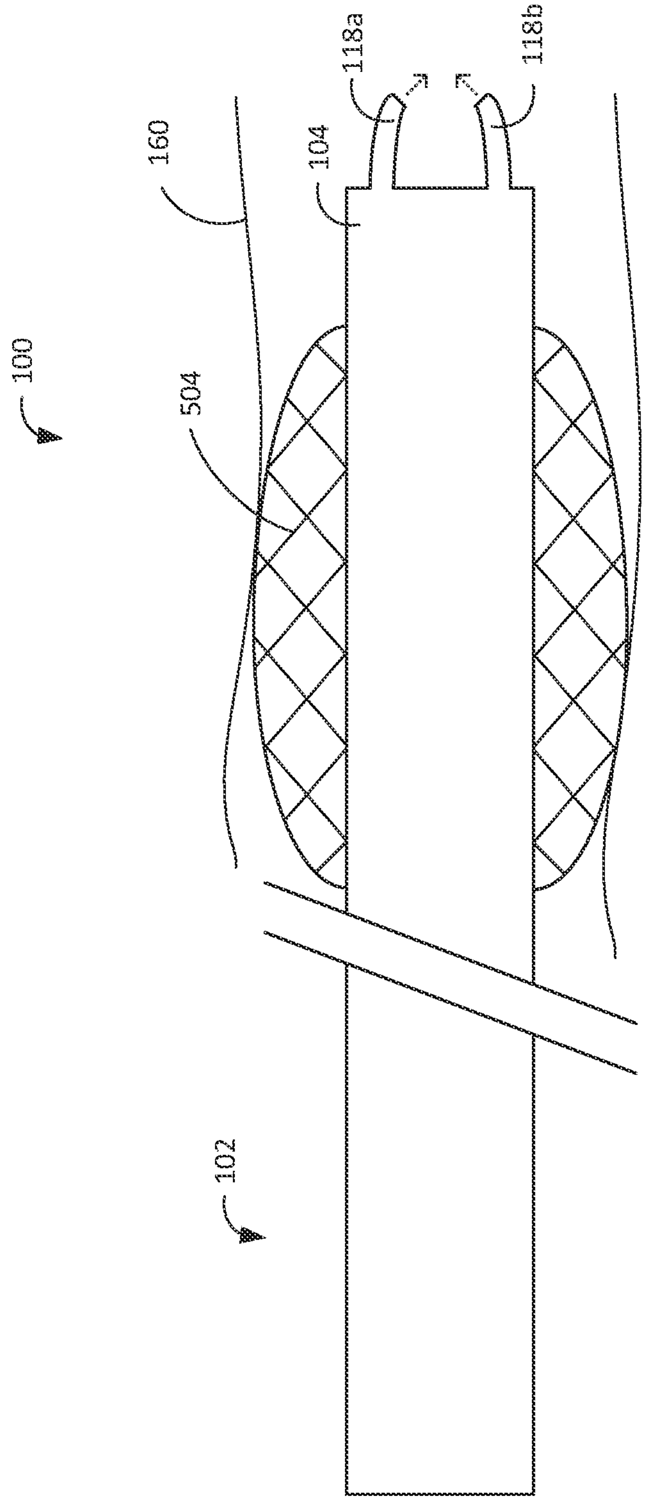
FIG. 5B is a diagram of an example catheter including an expandable mesh structure.

As another example, FIG. 5B shows an example catheter 102 including an expandable mesh structure 504. The mesh structure 504 encircles a portion of the catheter 104, and can be selectively expanded and collapsed. For example, after a portion of the catheter 102 has been inserted into a vessel 160, the mesh structure 504 can be expanded such that it contacts the walls of the vessel 160. In this configuration, the catheter 104 body is positioned centrally within the vessel 150. Accordingly, the streams of gas enriched liquid expelled by the capillaries 118*a* and 118*b* mix in a mixing region away from the walls of the vessel 160. As describe above, this can be beneficial, for example, in reducing mechanical stress on the walls of the vessel and in further suppressing preventing, or reducing the formation of bubbles.

As described above, the capillaries of a catheter can be configured such that the streams of gas enriched liquid expelled by the capillaries mix in a mixing region within the vasculature of the patient. For example, the capillaries can define respective paths that are angled relative to the longitudinal axis of the catheter, such that the streams are expelled from the capillaries at respective angles relative to the longitudinal axis 106. In some implementations, this angle can be from 10 degrees to 80 degrees or from 15 degrees to 75 degrees.

In some implementations, this angle can be selectively adjusted. For example, one or more of the capillaries can include a flexible portion or hinge that can be selectively bent or curved (e.g., to selectively increase or decrease the angle). This can be beneficial, for example, in enabling a user to adjust the distance between the mixing region and the end of the catheter.

Figure 6A:
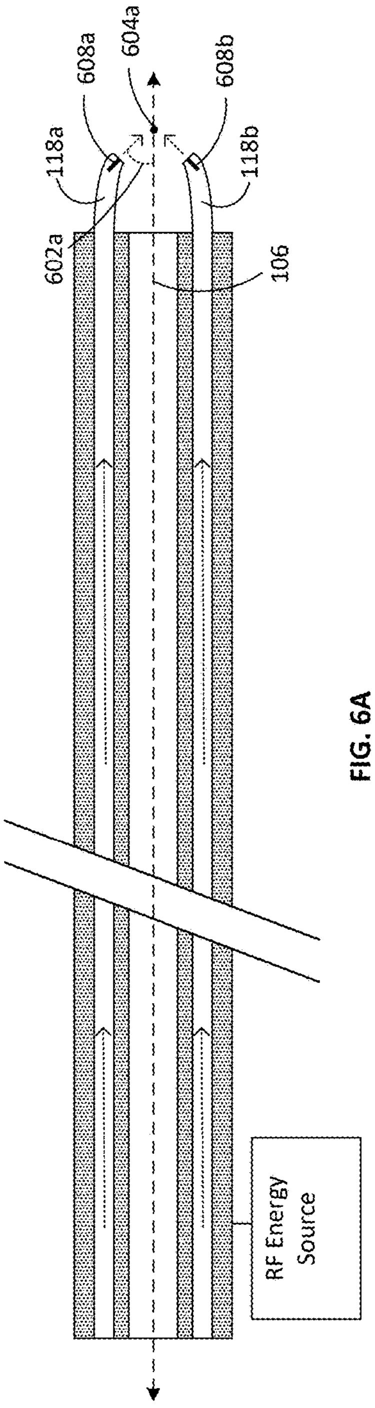
FIGS. 6A-6C are diagrams showing example configurations of the capillaries of a catheter.

For example, as shown in FIG. 6A, a catheter 102 can include two capillaries 118*a* and 118*b* (e.g., as described in connection with FIGS. 1A and 1B). Further, the capillaries 118*a* and 118*b* can define respective paths that are angled relative to the longitudinal axis 106 of the catheter 102 by a first angle 602*a*, such that the streams are expelled from the capillaries according to the first angle 602*a* relative to the longitudinal axis 106. For example, the capillaries 118*a* and 118*b* can define respective paths that are angled relative to the longitudinal axis 106 of the catheter 102 by a first angle 602*a* of about 45 degrees. In this configuration, the streams expelled by the capillaries 118*a* and 118*b* intersect at a first point 604*a* beyond the tip of the catheter 102.

Figure 6B:
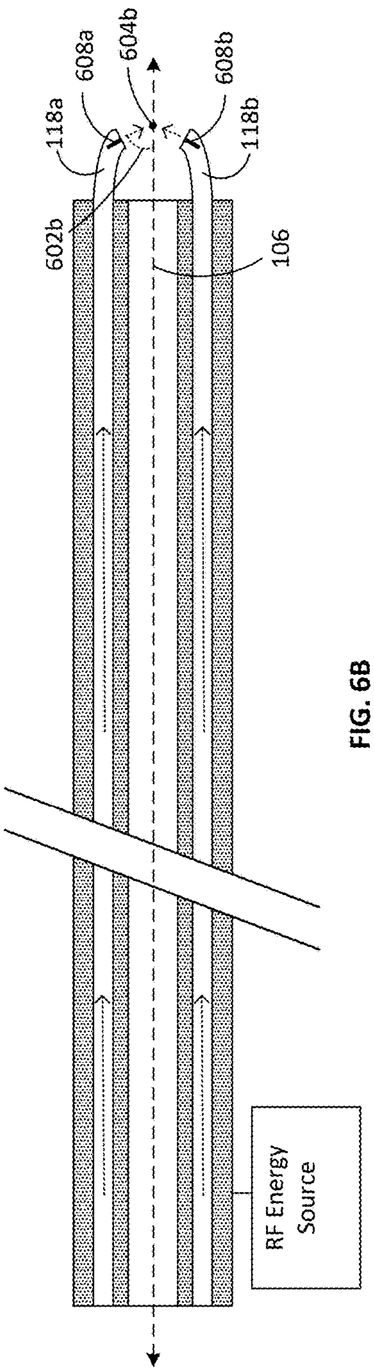

Further, as shown in FIG. 6B, the capillaries 118*a* and 118*b* can be adjusted, such that they define respective paths that are angled relative to the longitudinal axis 106 of the catheter 102 by a second angle 602*b*, where the second angle 602*b* is greater than the first angle 602*a*. Accordingly, the streams are expelled from the capillaries according to the second angle 602*b* relative to the longitudinal axis 106. For example, the capillaries 118*a* and 118*b* can define respective paths that are angled relative to the longitudinal axis 106 of the catheter 102 by a second angle 602*b* of about 60 degrees. In this configuration, the streams expelled by the capillaries 118*a* and 118*b* intersect at a second point 604*b* beyond the tip of the catheter 102. As shown in FIG. 6B, the distance between the second point 604*b* and the tip of the catheter 102 is less than the distance between the first point 604*a* and the tip of the catheter 102.

Figure 6C:
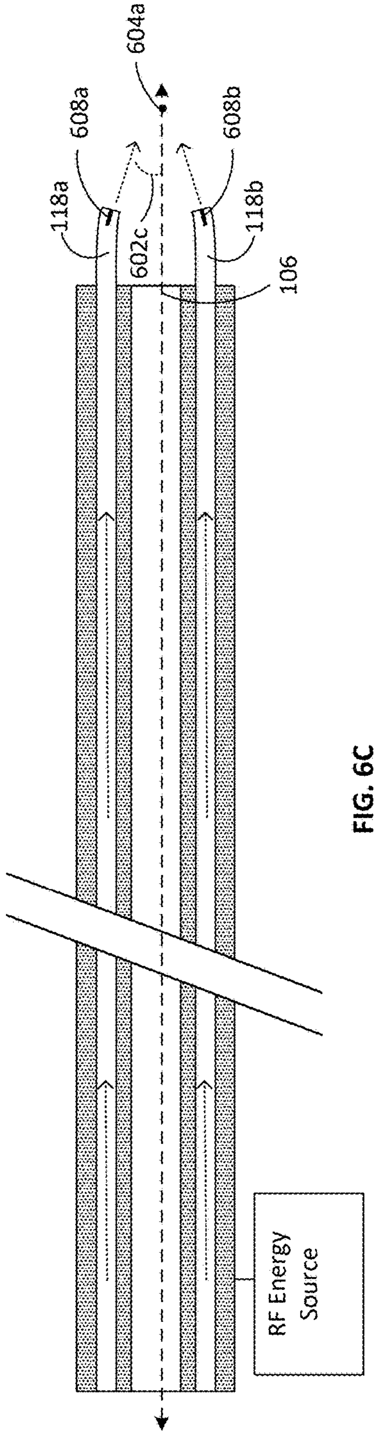

Further, as shown in FIG. 6C, the capillaries 118*a* and 118*b* can be adjusted, such that they define respective paths that are angled relative to the longitudinal axis 106 of the catheter 102 by a third angle 602*c*, where the third angle 602*c* is less than the first angle 602*a*. Accordingly, the streams are expelled from the capillaries according to the third angle 602*c* relative to the longitudinal axis 106. For example, the capillaries 118*a* and 118*b* can define respective paths that are angled relative to the longitudinal axis 106 of the catheter 102 by a third angle 602*c* of about 30 degrees. In this configuration, the streams expelled by the capillaries 118*a* and 118*b* intersect at a third point 604*c* beyond the tip of the catheter 102. As shown in FIG. 6C, the distance between the third point 604*c* and the tip of the catheter 102 is greater than the distance between the first point 604*a* and the tip of the catheter 102.

In some implementations, the catheter 102 can include features that enable a user to determine the orientation of the capillaries when it is inside the patient's body. For example, the capillaries 118*a* and 118*b* can include fiducial markings or structures that allow for manipulation or movement of the capillaries. For example, the structures may include a wire or other mechanism coupled to the capillary through the catheter to allow for manipulation or bending of the capillary. The bendable capillary can allow a user to define or modify the angle of respective jet stream paths relative to the longitudinal axis 106 of the catheter 102. Further, the fiducial markings on the capillaries can be used for positioning or guiding the capillaries. The fiducial markings can be composed, at least in part, of a radiopaque material (e.g., a metal or metal alloy), such that the orientation of the fiducial markings can be determined using a medical imaging system (e.g., an X-ray imaging system). For example, the fiducial markings may include radiopaque markers 608*a* and 608*b* shown in FIG. 6A, positioned on the capillaries 118*a* and 118*b*, respectively.

Figure 7A:
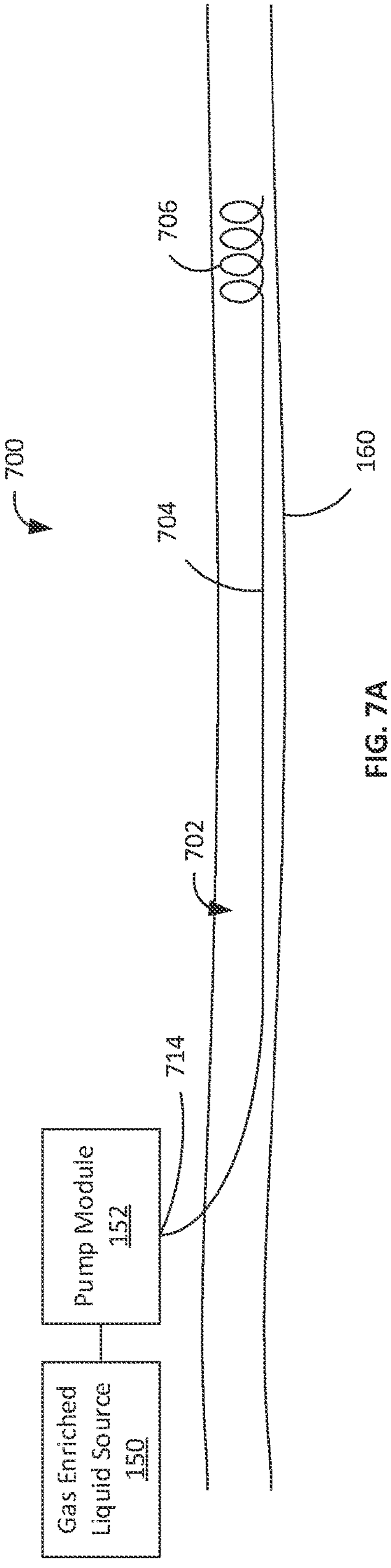
FIGS. 7A-7C are diagrams of another example system for enriching a bodily liquid with a gas-enriched liquid inside of an enclosed area of a body.

FIG. 7A shows another example system 700 for enriching a bodily liquid with a gas-enriched liquid inside of an enclosed area of a body. As an example, the system 100 can be used to enrich a patient's blood with supersaturated oxygen enriched liquid within the vasculature of the patient.

As shown in FIG. 7A, the system 700 includes a catheter 702, a gas enriched liquid source 150, and a pump 152. The catheter 702 is configured to be inserted into the vasculature of a patient, and is configured to facilitate the delivery of a gas enriched liquid (e.g., from the gas enriched liquid source 150) into the vasculature of the patient via the pump 152.

Figure 7B:
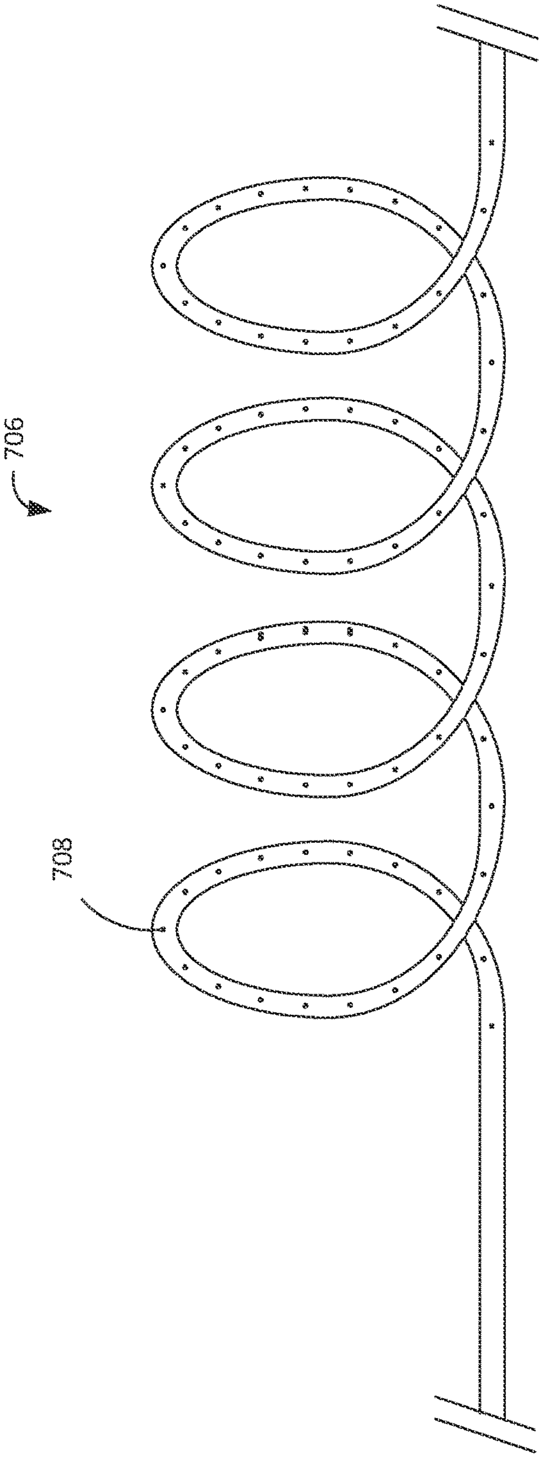

The catheter 102 includes an elongated tubular catheter body 704 having a coiled portion 706 (shown in greater detail in FIG. 7B). Further, the coiled portion 706 defines multiple output apertures 708 along at least a portion of its length. In some implementations, at least a portion of the catheter 702 and/or the catheter body 704 can be composed of polycarbonate, glass, ceramic, stainless steel, PEEK, and/or polyimide. In some implementations, the catheter body 174 can have an outer diameter ranging from 4 F to 12 F, or for example, 4 F to 5 F (according to the French scale). In some implementations, the catheter body 174 can have an inner diameter ranging from 0.020 inches to 0.045 inches (about 0.5 mm to about 1.1 mm).

Figure 7C:
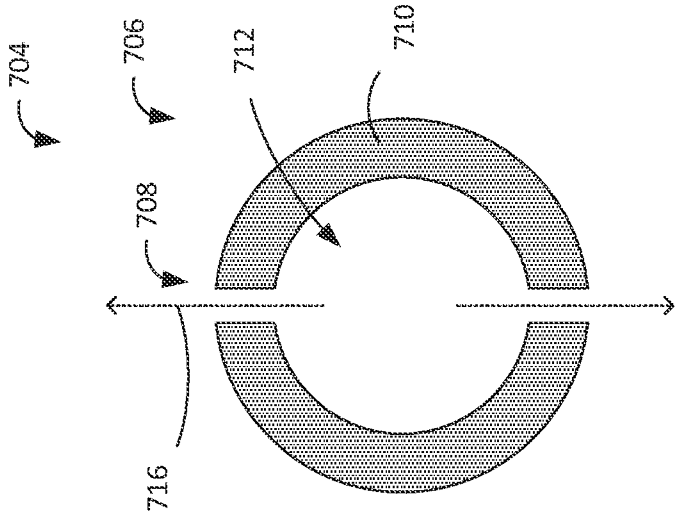

FIG. 7C shows a cross-sectional view of the coiled portion 706. As shown in FIG. 7C, the catheter body 704 includes a tubular wall 710 (e.g., having a circular, elliptical, or ovular cross section) that defines a lumen 712. Further, each of the output apertures 708 extends through the wall 710, such that a fluid path extends from the lumen 712 into the surrounding environment. In some implementations, the catheter 702 can extend in an axial direction, and at least some of the output apertures 708 can fan one or more radial directions orthogonal to the axial direction (e.g., such that streams of the gas enriched liquid are expelled from the catheter 702 in a direction orthogonal to a flow of blood in the patient's vasculature.

During an example usage of the system 700, the gas enriched liquid source 150 and the pump 152 are attached to the catheter 702, such that the gas enriched liquid source 150 and the pump 152 are in fluid communication with the lumen 712. As an example, one or more fluid-tight tubes can be used to convey gas enriched liquid from the gas enriched liquid source 150 to the pump 152, and from the pump 152 to an input aperture 714 of the catheter 702. In some implementations, the tubes can be secured to the input aperture 714 using a fitting or connector, such as a high-pressure Luer fitting.

Further, a portion of the catheter 702 is inserted into a patient, such as the coiled portion 706 of the catheter body 704 is positioned within a vasculature of a patient (e.g., a blood vessel 160, such as a vein or artery). After the catheter 702 has been inserted into the patient, the pump 152 is activated, such that it draws a gas enriched liquid from the gas enriched liquid source 150, and pumps the gas enriched liquid into the lumen 712. The gas enriched liquid flows through the lumen 712 and is expelled from the output apertures 708 and into the vessel 160 as respective streams 716, whereby it mixes with the blood in the vessel 160. This configuration can be beneficial, for example, in providing the gas enriched liquid into the blood of the patient in a diffuse manner, thereby eliminating or otherwise reducing the formation of bubbles within the vasculature of the patient.

Although FIGS. 7A and 7B show an example configuration of the coiled portion 706 having four coils, this is merely an illustrative example. In practice, the coiled portion 706 can have any number of coils (e.g., one, two, three, four, five, or more). Further, the coiled portion 706 can include any number of output apertures 708 (e.g., one, two, three, four, five, or more).

In some implementations, one of more of the coils in the coiled portion 706 can having a helical shape or a spiral shape (e.g., having a variable diameter). In some implementations, the coils in the coiled portion 706 can repeat according to a periodic pattern. In some implementations, the elongated tubular catheter body can be substantially straight, without a coiled or helical portion.

In some implementations, at least some of the output apertures 708 can be distributed periodically along at least a portion of the catheter body 704. In some implementations, adjacent output apertures 708 can be separated from one another by at least a particular minimum distance. The minimal distance can depend on the jet penetration of each of the streams expelled from the output apertures 708 (e.g, which can depend on the flow rate of the gas enriched liquid and/or the diameter of the output apertures 708). The output apertures may be spaced or distanced such that the jet penetration dissipates before reaching an adjacent output aperture or output aperture branch to prevent or reduce nucleation or bubble formation. For example, if the jet penetration is higher, the minimum spacing may be longer. As another example, if the jet penetration is lower, the minimum spacing may be shorter. This can be beneficial, for example, in further preventing or reducing the likelihood of the formation of bubbles due to nucleation. Example ranges for minimum spacing distance between output apertures include: 1 cm to 5 cm from aperture center to aperture center, either around the circumference of a catheter or along the longitudinal axis. In some implementations, adjacent apertures 708 can be offset or spaced from one another along the catheter body 704 by a distance that ranges from 1 cm to 5 cm.

Figure 8A:
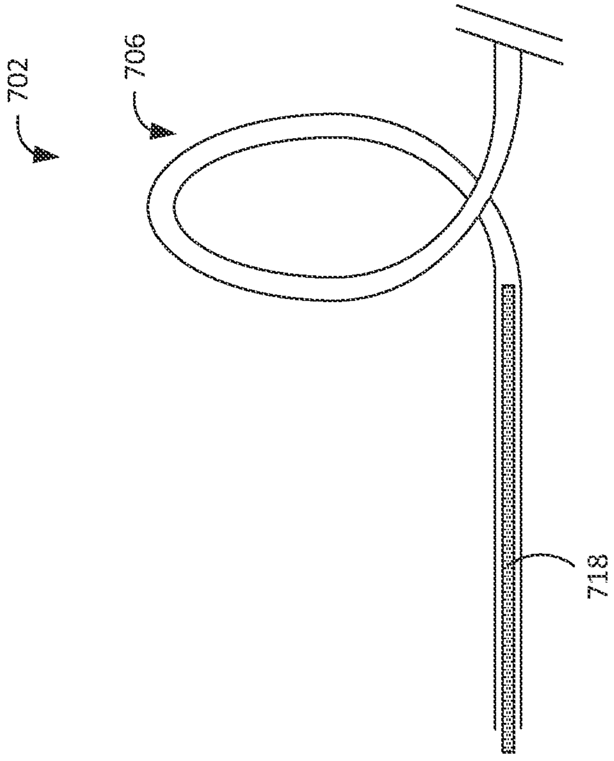
FIGS. 8A and 8B are diagrams showing an insertion of a guiding rod into an example catheter.
Figure 8B:
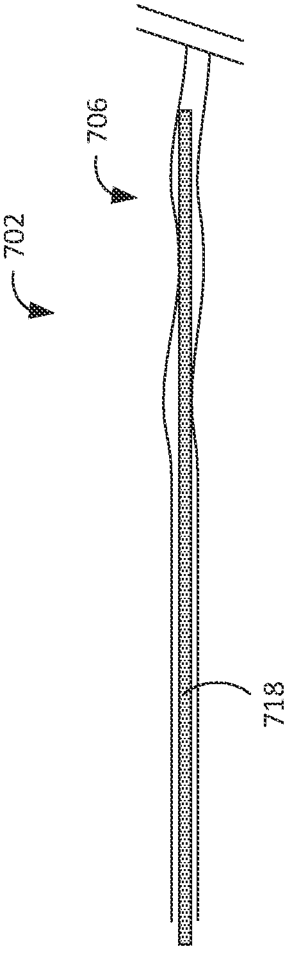

In some implementations, at least a portion of the catheter 702 can be flexible. This can be beneficial, for example, in facilitating the insertion and positioning of the catheter 702 within the body of the patient. As an example, as shown in FIG. 8A, a guiding rod 718 can be inserted into the lumen 712 of the catheter 702, and pushed towards the coiled portion 706. As shown in FIG. 8B, the guiding rod 718 can be pushed through at least a portion of the coiled portion 706, such that the coiled portion 706 is at least partially straightened. In this configuration, the catheter 702 can be inserted more easily into the vessel of the patient. Upon insertion of the catheter 702 into the vessel of the patient, the guiding rod 718 can be withdrawn from the catheter 702. In some implementations, the catheter 702 can be composed, at least in part, of a shape memory material, such that the coiled portion 706 returns to its coiled shape upon the withdrawal of the guiding rod 718.

Figure 9A:
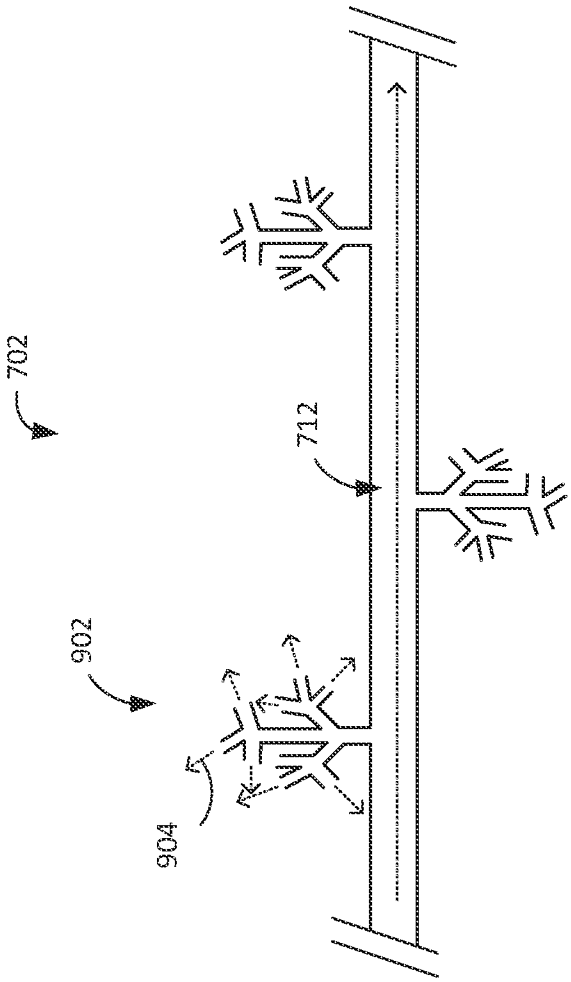
FIG. 9A is a diagram of an example catheter having tubular branching structures.

In the example shown in FIGS. 7A-7C, the catheter 702 includes multiple output apertures 708 in fluid communication with the lumen 712 of the catheter body 704 to the surrounding environment. However, in some implementations, the catheter 702 can further include one or more tubular structures to further increase the diffusivity by which the gas enriched liquid is expelled into the vasculature of the patient. For example, as shown in FIG. 9A, a catheter 702 can include one or more branching tubular structures 902, each configured to receive the gas enriched liquid from the lumen 712, and expel the gas enriched liquid into the vasculature of the patient as respective streams 904.

Figure 9B:
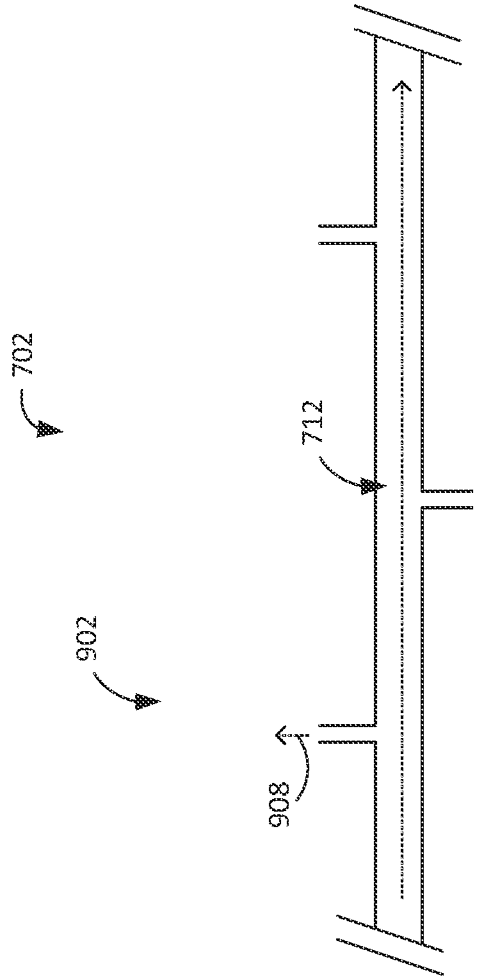
FIG. 9B is a diagram of an example catheter having tubular structures.

As another example, as shown in FIG. 9B, a catheter 702 can include one or more non-branching tubular structures 906, each configured to receive the gas enriched liquid from the lumen 712, and expel the gas enriched liquid into the vasculature of the patient as respective streams 908. In some implementations, a catheter can include both branching tubular structures and non-branching tubular structures. The tubular structures may be offset or spaced from one another along the longitudinal axis of the catheter to prevent a stream from a first tubular structure intersecting with a surface of a second tubular structure, to thereby reduce or prevent bubble formation or nucleation.

In general, the catheters 702 shown in FIGS. 9A and 9B can be similar to one or more of the other catheters described above (e.g., the catheters 702 described with reference to FIGS. 7A-7C). For example, the catheters 702 shown in FIGS. 9A and 9B can have an inner diameter that ranges from 0.020 inches to 0.045 inches (about 0.5 mm to about 1.1 mm), and/or an outer diameter that ranges from 4 F to 12 F (about 1.33 mm to 4 mm). Further, the catheters 702 shown in FIGS. 9A and 9B can include one or more fiducial markings. Further, one or more fluid-tight tubes can be used to convey gas enriched liquid from a gas enriched liquid source (e.g., the gas enriched liquid source 150) to a pump (e.g., the pump 152), and from the pump to an input aperture of the catheter 702. In some implementations, the tubes can be secured to the input aperture using a fitting or connector, such as a high-pressure Luer fitting.

In some implementations, at least some of the tubular structures 902 and/or 906 can dimensions that are identical to those another tubular structure. In some implementations, at least some of the tubular structures 902 and/or 906 can dimensions that are different from those another tubular structure. In some implementations, at least some of the tubular structures 902 and/or 906 can have an inner diameter that ranges from 40 microns to 100 microns. Further, at least some of the tubular structures 902 and/or 906 can have an outer diameter that ranges from 140 microns to 400 microns. In some implementations, adjacent tubular structures 902 and/or 906 can vary in length from one another by a length that ranges from 1 cm to 5 cm. In some implementations, adjacent tubular structures can offset or spaced from one another along the catheter body by a distance that ranges from 1 cm to 5 cm.

While this specification contains many details, these should not be construed as limitations on the scope of what may be claimed, but rather as descriptions of features specific to particular examples. Certain features that are described in this specification in the context of separate implementations can also be combined. Conversely, various features that are described in the context of a single implementation can also be implemented in multiple embodiments separately or in any suitable sub-combination.

A number of embodiments have been described. Nevertheless, various modifications can be made without departing from the spirit and scope of the invention. Accordingly, other embodiments are within the scope of the claims.

What is claimed is:

1. A catheter configured to be inserted into a vasculature of a patient, wherein the catheter comprises:

a catheter body, a first lumen extending through the catheter body, wherein the first lumen is configured to be in fluid communication with the vasculature of the patient when the catheter is inserted into the vasculature of the patient, and the first lumen is configured to perform at least one of receiving a sample of blood from the vasculature of the patient or measuring a parameter of blood of the patient;

one or more second lumens extending through the catheter body, wherein the one or more second lumens are configured to receive a gas enriched liquid from a gas enriched liquid source; and two or more capillaries extending from the catheter body and coupled to the one or more second lumens, wherein each of the two or more capillaries are in fluid communication with the one or more second lumens and are in fluid communication with the vasculature of the patient when the catheter is inserted into the vasculature of the patient, and wherein each of the two or more capillaries are configured to receive the gas enriched liquid from the one or more second lumens and to simultaneously dispense respective streams of the gas enriched liquid directly into the vasculature of the patient, wherein the catheter body is configured to position the two or more capillaries at one or more predetermined angles relative to one another, such that the streams of the gas enriched liquid intersect and mix with the blood of the patient in a region beyond an end of the catheter body and beyond the first lumen, wherein the catheter body is configured to position the two or more capillaries such that the streams of the gas enriched liquid do not intersect a longitudinal axis extending through a center of the catheter.

2. The catheter of claim 1, further comprising a pressure sensor disposed within the first lumen, wherein the pressure sensor is configured to obtain one or more pressure measurements.

3. The catheter of claim 1, wherein the parameter of the blood of the patient is at least one of:

a partial pressure of oxygen of the blood of the patient, $SO_2$ of the blood of the patient, a pressure of the blood of the patient, a flow rate of the of the blood of the patient, or a temperature of the of the blood of the patient.

4. The catheter of claim 1, wherein the catheter comprises:

a third lumen extending through the catheter body, wherein the third lumen is configured to be in fluid communication with the vasculature of the patient when the catheter is inserted into the vasculature of the patient, and the third lumen is configured to perform at least one of receiving an additional sample of the blood of the patient from the vasculature of the patient and or measuring an additional parameter of the blood of the patient.

5. The catheter of claim 1, further comprising one or more shields or guards positioned over a distal opening of the first lumen and configured to reduce nucleation along one or more surfaces of the catheter.

6. The catheter of claim 1, wherein at least one capillary comprises a fiducial marking.

7. The catheter of claim 1, further comprising one or more sensors, wherein the one or more sensors are configured such that the one or more sensors are in fluid communication with the vasculature of the patient when the catheter is inserted into the vasculature of the patient.

8. The catheter of claim 7, wherein at least one of the one or more sensors is an oxygen partial pressure ($pO_2$) sensor.

9. The catheter of claim 1, further comprising a self-centering device configured to center the catheter body within the vasculature of the patient.

10. A system comprising:

a catheter body, a first lumen extending through the catheter body, wherein the first lumen is configured to be in fluid communication with a vasculature of a patient when the catheter body is inserted into the vasculature of the patient, and the first lumen is configured to perform at least one of receiving a sample of blood from the vasculature of the patient or measuring a parameter of the blood of the patient;

one or more second lumens extending through the catheter body, wherein the one or more second lumens are configured to receive a gas enriched liquid from a gas enriched liquid source; and two or more capillaries extending from the catheter body and coupled to the one or more second lumens, wherein each of the two or more capillaries are in fluid communication with the one or more second lumens and are in fluid communication with the vasculature of the patient when the catheter body is inserted into the vasculature of the patient, and wherein each of the two or more capillaries are configured to receive the gas enriched liquid from the one or more second lumens and to simultaneously dispense respective streams of the gas enriched liquid directly into the vasculature of the patient, wherein the catheter body is configured to position the two or more capillaries at one or more predetermined angles relative to one another, such that the streams of the gas enriched liquid do not intersect a longitudinal axis extending through a center of the catheter and mix with the blood of the patient in a region beyond an end of the catheter body and beyond the first lumen; and a fluid dispensing device in fluid communication with the one or more second lumens, wherein the fluid dispensing device comprises one or more pumps configured to provide the gas enriched liquid to the one or more second lumens.

11. The system of claim 10, further comprising one or more connectors configured to couple the one or more second lumens to one or more respective dispensing ports of the fluid dispensing device.

12. The system of claim 10, wherein the gas enriched liquid comprises one or more of oxygen, ozone, inert gas, nitrogen, nitrous oxide, carbon dioxide, or air.

13. The system of claim 10, further comprising a pressure sensor disposed within the first lumen, wherein the pressure sensor is configured to obtain one or more pressure measurements.

14. The system of claim 10, wherein the parameter of the blood of the patient is at least one of:

a partial pressure of oxygen of the blood of the patient, $SO_2$ of the blood of the patient, a pressure of the blood of the patient, a flow rate of the of the blood of the patient, or a temperature of the of the blood of the patient.

15. The system of claim 10, wherein the catheter comprises:

a third lumen extending through the catheter body, wherein the third lumen is configured to be in fluid communication with the vasculature of the patient when the catheter is inserted into the vasculature of the patient, and the third lumen is configured to perform at least one of receiving an additional sample of the blood of the patient from the vasculature of the patient and or measuring an additional parameter of the blood of the patient.

16. The catheter of claim 10, further comprising one or more sensors, wherein the one or more sensors are configured such that the one or more sensors are in fluid communication with the vasculature of the patient when the catheter is inserted into the vasculature of the patient.

17. A system comprising:

a catheter body, a first lumen extending through the catheter body, wherein the first lumen is configured to be in fluid communication with a vasculature of a patient when the catheter is inserted into the vasculature of the patient, and the first lumen is configured to perform at least one of receiving a sample of blood from the vasculature of the patient or measuring a parameter of the blood of the patient;

one or more second lumens extending through the catheter body, wherein the one or more second lumens are configured to receive a gas enriched liquid from a gas enriched liquid source; and two or more capillaries extending from the catheter body and coupled to the one or more second lumens, wherein each of the two or more capillaries are in fluid communication with the one or more second lumens and are in fluid communication with the vasculature of the patient when the catheter body is inserted into the vasculature of the patient, and wherein each of the two or more capillaries are configured to receive the gas enriched liquid from the one or more second lumens and to simultaneously dispense respective streams of the gas enriched liquid directly into the vasculature of the patient, wherein the catheter body is configured to position the two or more capillaries at one or more predetermined angles relative to one another, such that the streams of the gas enriched liquid do not intersect a longitudinal axis extending through a center of the catheter and mix with the blood of the patient in a region beyond an end of the catheter body and beyond the first lumen; and a blood sampling device in fluid communication with the first lumen, wherein the blood sampling device is configured to withdraw the sample of the blood of the patient from the vasculature of the patient through the first lumen.

18. The catheter of claim 17, wherein the parameter of the blood of the patient is at least one of:

a partial pressure of oxygen of the blood of the patient, $SO_2$ of the blood of the patient, a pressure of the blood of the patient, a flow rate of the of the blood of the patient, or a temperature of the of the blood of the patient.

19. The catheter of claim 17, further comprising one or more sensors, wherein the one or more sensors are configured such that the one or more sensors are in fluid communication with the vasculature of the patient when the catheter is inserted into the vasculature of the patient.

* * * * *